United States Patent
Watnick

(10) Patent No.: US 11,466,080 B2
(45) Date of Patent: Oct. 11, 2022

(54) METHODS OF TREATING CANCER USING ANTI-LRP1 POLYCLONAL ANTIBODIES

(71) Applicant: Children's Medical Center Corporation, Boston, MA (US)

(72) Inventor: Randolph S. Watnick, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/496,129

(22) PCT Filed: Mar. 22, 2018

(86) PCT No.: PCT/US2018/023809
§ 371 (c)(1),
(2) Date: Sep. 20, 2019

(87) PCT Pub. No.: WO2018/175749
PCT Pub. Date: Sep. 27, 2018

(65) Prior Publication Data
US 2020/0024341 A1 Jan. 23, 2020

Related U.S. Application Data

(60) Provisional application No. 62/475,133, filed on Mar. 22, 2017.

(51) Int. Cl.
*A61K 39/395* (2006.01)
*A61P 35/00* (2006.01)
*C07K 16/28* (2006.01)

(52) U.S. Cl.
CPC .......... *C07K 16/28* (2013.01); *A61K 39/3955* (2013.01); *A61P 35/00* (2018.01)

(58) Field of Classification Search
CPC ...... C07K 16/28; A61K 39/3955; A61P 35/00
See application file for complete search history.

(56) References Cited

U.S. PATENT DOCUMENTS

| | | | |
|---|---|---|---|
| 5,976,809 A | 11/1999 | Stenman et al. | |
| 7,939,263 B2 | 5/2011 | Clarke et al. | |
| 10,736,935 B2 * | 8/2020 | Watnick | G01N 33/74 |
| 2013/0072425 A1 | 3/2013 | Watnick et al. | |
| 2014/0193426 A1 | 7/2014 | O'Brien et al. | |
| 2015/0320825 A1 * | 11/2015 | Watnick | C07K 5/1021 424/134.1 |
| 2020/0031906 A1 | 1/2020 | Watnick | |

FOREIGN PATENT DOCUMENTS

| | | |
|---|---|---|
| CN | 105586391 A | 5/2016 |
| EP | 2 322 204 A1 | 5/2011 |
| WO | WO 2004/110478 A1 | 12/2004 |
| WO | WO 2011/054644 A1 | 5/2011 |
| WO | WO 2011/061236 A1 | 5/2011 |
| WO | WO 2011/084685 A2 | 7/2011 |
| WO | WO 2012/088309 A1 | 6/2012 |
| WO | WO 2013/096868 A2 | 6/2013 |
| WO | WO 2009/002931 A2 | 12/2014 |

OTHER PUBLICATIONS

Lindner et al, 2010. Cancer Res; 70(1): 277-287.*
Jo et al., Wnt signaling can repress thrombospondin-1 expression in colonic tumorigenesis. Cancer Biol Ther. Dec. 2005;4(12):1361-6.
Kang et al., Prosaposin inhibits tumor metastasis via paracrine and endocrine stimulation of stromal p53 and Tsp-1. PNAS.Jul. 21, 2009;106(29):12115-20.
Li et al., Endogenous thrombospondin-1 is a cell-surface ligand for regulation of integrin-dependent T-lymphocyte adhesion. Blood. Nov. 1, 2006;108(9):3112-20.
Lillis et al., LDL receptor-related protein 1: unique tissue-specific functions revealed by selective gene knockout studies. Physiol Rev. Jul. 2008;88(3):887-918.
Lukkonen et al., Down-Regulation of Trypsinogen-2 Expression by Chemically Modified Tetracyclines: Association with Reduced Cancer Cell Migration. Int. J. Cancer. May 2000;86:577-81.
Mikhailenko et al., Recognition of alpha 2-macroglobulin by the low density lipoprotein receptor-related protein requires the cooperation of two ligand binding cluster regions. J Biol Chem. Oct. 19, 2001;276(42):39484-91.
Orr et al., Thrombospondin signaling through the calreticulin/LDL receptor-related protein co-complex stimulates random and directed cell migration. J Cell Sci. Jul. 15, 2003;116(Pt 14):2917-27.
Rinderknecht et al., Trypsinogen variants in pancreatic juice of healthy volunteers, chronic alcoholics, and patients with pancreatitis and cancer of the pancreas. Gut. Oct. 1979;20(10):886-91.
Van Gool et al., The Matricellular Receptor LRP1 Forms an Interface for Signaling and Endocytosis in Modulation of the Extracellular Tumor Environment. Front Pharmacol. Nov. 10, 2015;6:271.
U.S. Appl. No. 16/496,142, filed Sep. 20, 2019, Watnick.
EP 18770188.3, Nov. 23, 2020, Extended European Search Report.
PCT/US2018/023809, Jan. 11, 2019, International Search Report and Written Opinion.
PCT/US2018/023809, Oct. 3, 2019, International Preliminary Report on Patentability.
PCT/US2018/023809, Aug. 31, 2018, Invitation to Pay Additional Fees.
EP 187725585, Dec. 3, 2020, Extended European Search Report.
PCT/US2018/023830, Jul. 19, 2018, International Search Report and Written Opinion.
PCT/US2018/023830, Oct. 3, 2019, International Preliminary Report on Patentability.

* cited by examiner

*Primary Examiner* — Zachary C Howard
(74) *Attorney, Agent, or Firm* — Wolf, Greenfield & Sacks, P.C.

(57) ABSTRACT

Provided herein are agents that hind to binding domain I of LRP1 and mimic the activity of prosaposin in stimulating Tsp-1. Further provided herein are agents that inhibit the function (e.g., the ability to repress Tsp-1) of Protease, Serine 2 (PRSS2) by inhibiting the binding of PRSS2 to LRP1. Methods of using these agents in treating cancer are also provided.

10 Claims, 10 Drawing Sheets
Specification includes a Sequence Listing.

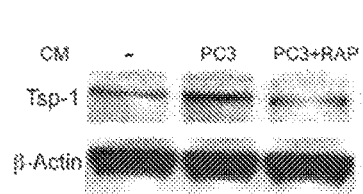
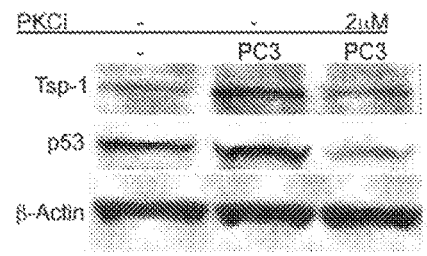
Figure 6A    Figure 6B
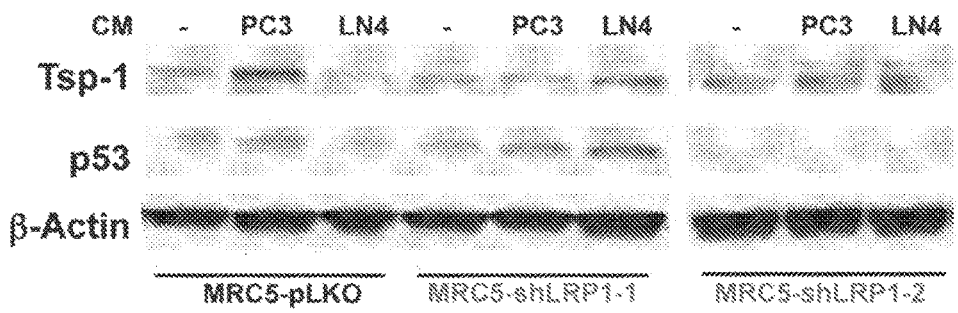
Figure 7
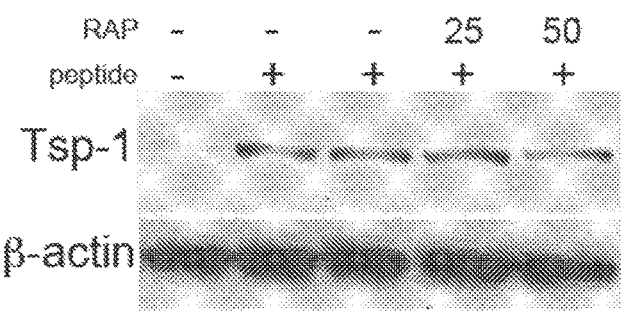
Figure 8A
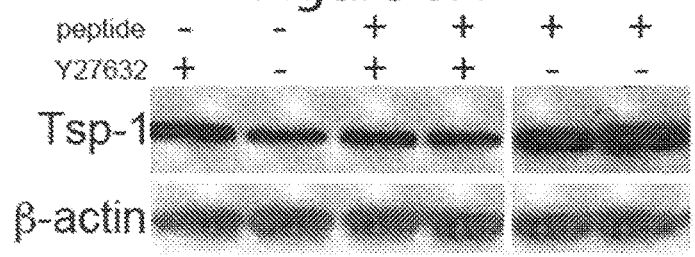
Figure 8B Co-immunoprecipitation of LRP1 peptides with PSAP Co-immunoprecipitation of LRP1 peptides with PRSS2

METHODS OF TREATING CANCER USING ANTI-LRP1 POLYCLONAL ANTIBODIES

RELATED APPLICATIONS

This application is a national stage filing under 35 U.S.C. § 371 of international application number PCT/US2018/023809, filed Mar. 22, 2018, which claims the benefit under 35 U.S.C. § 119(e) of U.S. Provisional Application No. 62/475,133 filed Mar. 22, 2017, the entire contents of each of which are incorporated herein by reference.

BACKGROUND

The current standard of care for cancer patients consists of broadly acting cytotoxic agents (chemotherapy), radiation, and directed therapeutics that target specific secreted proteins, cell surface receptors, or kinases. Historically, there have been two classes of therapeutics that target the tumor microenvironment, anti-angiogenic drugs (which have been limited to anti-VEGF therapies) and immunomodulatory drugs. One of the major drawbacks to therapies that target the microenvironment is that they do not have direct anti-tumor activity and thus their efficacy as monotherapies has been limited. Conversely, a major drawback of targeted therapies and chemotherapies that have direct anti-tumor activity is that patients develop resistance to the drug, in addition to unintended deleterious side effects.

SUMMARY

Provided herein are novel cancer therapeutic strategies that possess both anti-cancer activity and target the cancer microenvironment to prevent cancer reoccurrence and/or metastasis, by stimulating the activity of the potent anti-angiogenic and anti-tumorigenic protein Thrombospondin 1 (Tsp-1).

Some aspects of the present disclosure provide methods of treating cancer, the method comprising administering to a subject in need thereof an effective amount of an agent that binds to binding domain I of Low Density Lipoprotein Receptor-related Protein 1 (LRP1).

In some embodiments, binding domain I of LRP1 comprises amino acids 1-172 of LRP1. In some embodiments, the agent is a protein or peptide.

In some embodiments, the agent is an antibody. In some embodiments, the antibody is a polyclonal antibody. In some embodiments, the antibody is a monoclonal antibody. In some embodiments, the antibody hinds to amino acids 151-172 (SEQ ID NO: 3) in the binding domain I of LRP1.

In some embodiments, the agent is a small molecule. In some embodiments, the small molecule is selected from the group consisting of: lipids, monosaccharides, second messengers, metabolites, and xenobiotics.

In some embodiments, binding of the agent to binding domain I of LRP1 activates a Rho-GTPase pathway. In some embodiments, the Rho pathway is a LRP-1 mediated Rho-GTPase pathway. In some embodiments, binding of the agent to binding domain I of LRP1 stimulates Thrombospondin 1 (Tsp-1).

In some embodiments, the agent is administered orally, parenterally, intramuscularly, intranasally, intratracheally, intracerebroventricularly, intravenously, or intraperitoneally.

In some embodiments, the cancer is metastatic. In some embodiments, the cancer is biliary tract cancer; bladder cancer; brain cancer; glioblastoma; medulloblastoma; breast cancer; cervical cancer; choriocarcinoma; colon cancer; endometrial cancer: esophageal cancer; gastric cancer; hematological neoplasm; acute lymphocytic and myelogenous leukemia; multiple myeloma; AIDS-associated leukemias and adult T-cell leukemia, lymphoma; intraepithelial neoplasm; Bowen's disease; Paget's disease; liver cancer; lung cancer; lymphomas; Hodgkin's disease; lymphocytic lymphoma; neuroblastomas; oral cancer; squamous cell carcinoma; ovarian cancer; pancreatic cancer; prostate cancer; rectal cancer; sarcomas; leiomyosarcoma; rhabdomyosarcoma; liposarcoma; fibrosarcoma; osteosarcoma; skin cancer; testicular cancer; stromal tumors and germ cell tumors; thyroid cancer; and renal cancer. In some embodiments, the cancer is prostate cancer, breast cancer, ovarian cancer, or pancreatic cancer.

Other aspects of the present disclosure provide antibodies bind binding domain I of Low Density Lipoprotein Receptor-related Protein 1 (LRP1). In some embodiments, binding domain I of LRP-1 comprises the amino acids 1-172 of LRP-1. In some embodiments, the antibody binds to amino acids 151-172(SEQ ID NO: 3) in binding domain I of LRP1.

In some embodiments, the antibody is a polyclonal antibody. In some embodiments, the antibody is a monoclonal antibody. In some embodiments, the antibody stimulates Tsp-1.

Further provided herein are methods of treating cancer, the method comprising administering to a subject in need thereof an effective amount of an agent that stimulates Thrombospondin 1 (Tsp-1). In some embodiments, the agent inhibits the ability of Protease, serine 2 (PRSS2) to repress Tsp-1. In some embodiments, the agent binds to binding domain I of LRP1. In some embodiments, the agent inhibits binding of PRSS2 to Low density lipoprotein receptor-related protein 1 (LRP1).

Further provided herein are methods of treating cancer, the method comprising administering to a subject in need thereof an effective amount of a first agent that inhibits the function of Protease, serine 2 (PRSS2), and an effective amount of a second agent that binds to binding domain I of Low density lipoprotein receptor-related protein I (LRP1). In some embodiments, the first agent and the second agent are administered simultaneously. In some embodiments, the first agent and the second agent are administered sequentially.

The details of one or more embodiments of the disclosure are set forth in the description below. Other features or advantages of the present disclosure will be apparent from the following drawings and detailed description of several embodiments, and also from the appending claims.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein. In the drawings:

FIGS. 6A-6B. Western blot analysis of: (FIG. 6A) Tsp-1 and β-actin expression in prostate fibroblasts that were untreated (−) or treated with conditioned media from PC3 cells alone or in combination with RAP, and (FIG. 6B) Tsp-1, p53 and β-actin expression in prostate fibroblasts that were untreated (−) or treated with conditioned media from PC3 cells alone or in combination with the PKC inhibitor Gδ 6983 (PKCi).

FIG. 7. Western blot analysis of Tsp-1, p53 and β-actin expression in MRC5 lung fibroblasts that were transduced with an empty vector (pLKO) or lentiviral vectors expressing two independent shRNA sequences specific for LRP1, which were untreated (−) or treated with conditioned media from PC3 cells or PC3M-LN4 cells.

FIGS. 8A-8B. Western blot analysis of Tsp-1 and β-actin expression in lung fibroblasts, which were (FIG. 8A) untreated (−) or treated with psap peptide alone or in combination with 25 or 50 μg of rhRAP, and (FIG. 8B) untreated (−) or treated with psap peptide alone or with Y27632.

(FIG. 13A) Schematic diagram of mini-LRP1 receptors. (FIG. 13B) Western blot analysis of Tsp-1, miniLRP and β-actin expression in 293T cells that were untreated (−) or treated the cyclic prosaposin peptide.

DETAILED DESCRIPTION OF CERTAIN EMBODIMENTS

Figure 1:
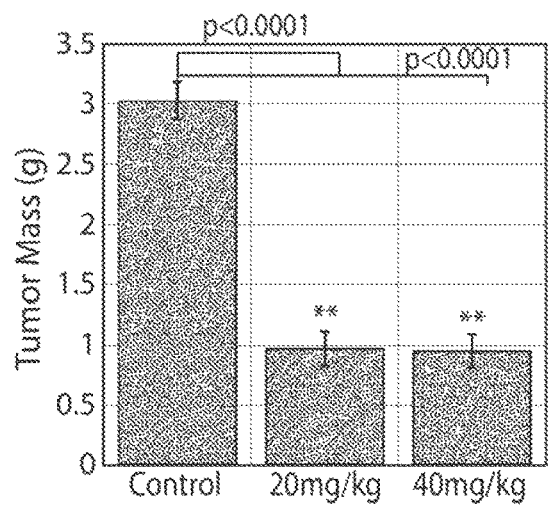
FIG. 1. Plot of average tumor mass of AsPc1 tumors treated with vehicle control or peptide at a dose of 20 and 40 mg/kg/day.

Provided herein are novel cancer therapeutic strategies that possess both anti-cancer activity and ability to target the cancer microenvironment to prevent cancer reoccurrence and/or metastasis. The anti-cancer strategies described herein rely, at least in part, on stimulating the activity of a potent anti-angiogenic and anti-tumorigenic protein, Thrombospondin 1 (Tsp-1). "Tsp-1" is a subunit of a disulfide-linked homotrimeric protein. Tsp-1 is an adhesive glycoprotein that mediates cell-to-cell and cell-to-matrix interactions. Tsp-1 binds to fibrinogen, fibronectin, laminin, type V collagen and integrins alpha-V/beta-1 and has been shown to play roles in platelet aggregation, angiogenesis, and tumorigenesis. For the purpose of the present disclosure. Tsp-1 is a potent anti-tumorigenic and anti-angiogenic factor, whose activation suppresses tumor growth and metastasis and represses angiogenesis in the tumor microenvironment.

Prosaposin or prosaposin-derived peptides were previously shown to be able to stimulate the activity of Tsp-1 and are effective for treating multiple types of cancers (see, e.g., PCT publications WO2009002931 WO/2011/084685 and WO12013/096868, WO2015148801 and U.S. patent application Ser. Nos. 12/640,788 and 13/516,511, all of which are incorporated herein by reference in their entirety).

The present disclosure is based, at least in part, on the finding that the stimulating activity of prosaposin or a prosaposin-derived peptide to Tsp-1 is mediated by the Low Density Lipoprotein Receptor Related Protein 1 (LRP1.). "Low Density Lipoprotein Receptor Related Protein 1 (LRP1)," also known as alpha-2-macroglobulin receptor (A2MR), apolipoprotein E receptor (APOER) or cluster of differentiation 91 (CD91), is a protein forming a receptor found in the plasma membrane of cells involved in receptor-mediated endocytosis. In humans, LRP1 is encoded by the LRP1 gene. LRP1 is a key signaling protein and is involved in various biological processes, such as lipoprotein metabolism and cell motility, and diseases, such as neurodegenerative diseases, atherosclerosis, and cancer.

The LRP1 gene encodes a 600 kDa precursor protein that is processed by furin in the trans-Golgi complex, resulting in a 515 kDa alpha-chain and an 85 kDa beta-chain associated noncovalently. As a member of the LDLR family, LRP1 contains cysteine-rich complement-type repeats, EGF (gene) repeats, β-propeller domains, a transmembrane domain, and a cytoplasmic domain. The cytoplasmic domain of LRP1 is the alpha-chain, which comprises four ligand-binding domains (termed "binding domains I-IV") containing two, eight, ten, and eleven cysteine-rich complement-type repeats, respectively. These repeats bind extracellular matrix proteins, growth factors, proteases, protease inhibitor complexes, and other proteins involved in lipoprotein metabolism. Of the four domains, II and IV bind the majority of the protein's ligands. The EGF repeats and β-propeller domains serve to release ligands in low pH conditions, such as inside endosomes, with the β-propeller postulated to displace the ligand at the ligand binding repeats. The transmembrane domain is the β-chain, which contains a 100-residue cytoplasmic tail. This tail contains two NPxY motifs that are responsible for the protein's function in endocytosis and signal transduction.

To date, no ligand has been identified that binds to binding domain I of LRP1, described herein, binding domain I of LRP1 comprises about amino acids 1-200 of LRP1 and contains the first two β-propeller domains of LRP1. "About" means the binding domain I of LRP1 may be no more than 15% longer or shorter than 200 amino acids. For example, the binding domain I of LRP1 may comprise amino acids 1-200, 1-199, 1-198, 1-197, 1-196, 1-195, 1-194, 1-193, 1-192, 1-191, 1-190, 1-189, 1-188, 1-187, 1-186, 1-185, 1-184, 1-183, 1-182, 1-181, 1-180, 1-179, 1-178, 1-177, 1-176, 1-175, 1-174, 1-173, 1-172, 1-171, 1-170, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, or 1-230 of the LRP1 protein. In some embodiments, the binding domain I of LRP1 comprises amino acids 1-172 of the LRP1 protein.

Figure 13A:
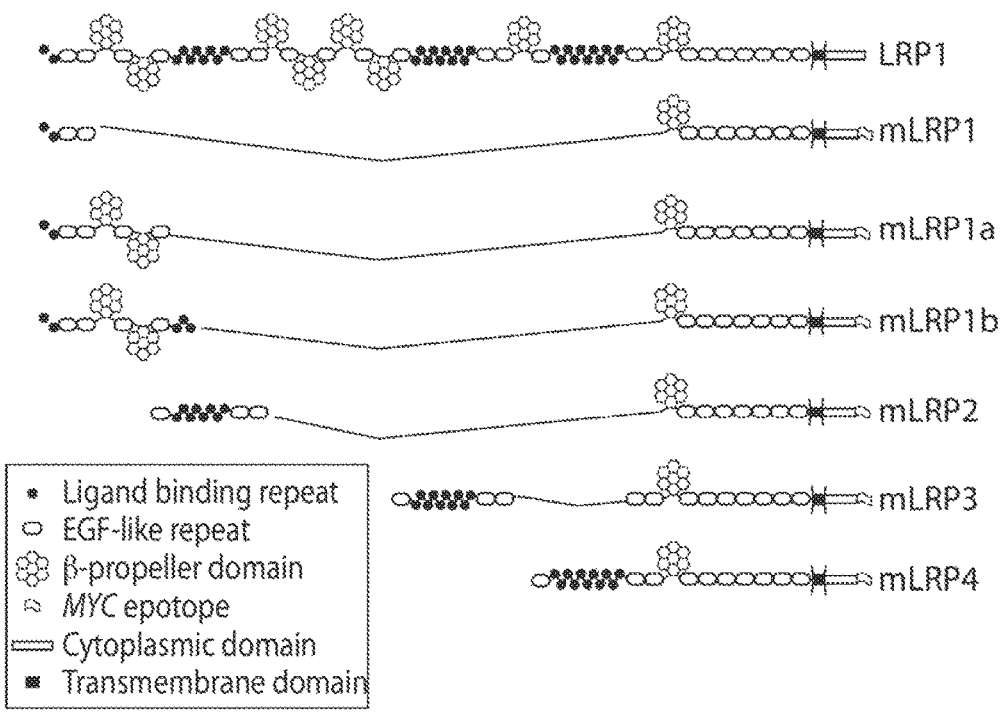
FIGS. 13A-13B.

The present disclosure further provides the identification of ligands that bind to binding domain I of LRP1. As demonstrated in the Figures and Examples of the present disclosure, prosaposin or prosaposin-derived peptides were found to bind to the binding domain I of LRP1 and the binding of the prosaposin-derived peptide activates Tsp1 and represses cancer (e.g., FIGS. 13A and 13B). Another ligand of the binding domain I of LRP1 identified in the present disclosure is Protease, serine 2 (PRSS2) (e.g., FIG. 10). "PRSS2" is a trypsinogen and is a member of the trypsin family of serine proteases. PRSS2 is secreted by the pancreas and cleaved to its active form in the small intestine. It is active on peptide linkages involving the carboxyl group of lysine or arginine. As demonstrated herein, PRSS2 represses the activity of Tsp-1 in the tumor microenvironment and thus promotes the progression of cancer. The ability of PRSS2 to repress Tsp-1 is mediated by binding of PRSS2 to binding domain I of the LRP-1 protein.

Accordingly, some aspects of the present disclosure provide agents that bind to the binding domain I of LRP1. Such agents mimic the activity of prosaposin or prosaposin-derived peptides and activates Tsp-1 when bound to binding domain I of LRP1. In some embodiments, the agent binds to a peptide within amino acids 1-172 of the LRP1 protein. In some embodiments, the agent binds to a peptide within the region of amino acids 140-180 of the LRP1 protein. For example, without limitation, the agent may bind to amino acids 140-180, 140-179, 140-178, 140-177, 140-176, 140-175, 140-174, 140-173, 140-172, 140-171, 140-170, 140-169, 140-168, 140-167, 140-166, 140-165, 140-164, 140-163, 140-162, 140-161, 140-160, 141-180, 141-179, 141-178, 141-177, 141-176, 141-175, 141-174, 141-173, 141-172, 141-171, 141-170, 141-169, 141-168, 141-167, 141-166, 141-165, 141-164, 141-163, 141-162, 141-161, 142-180, 142-179, 142-178, 142-177, 142-176, 142-175, 142-174, 142-173, 142-172, 142-171, 142-170, 142-169, 142-168, 142-167, 142-166, 142-165, 142-164, 142-163, 142-162, 143-180, 143-179, 143-178, 143-177, 143-176, 143-175, 143-174, 143-173, 143-172, 143-171, 143-170, 143-169, 143-168, 143-167, 143-166, 143-165, 143-164, 143-163, 144-180, 144-179, 144-178, 144-177, 144-176, 144-175, 144-174, 144-173, 144-172, 144-171, 144-170, 144-169, 144-169, 144-168, 144-167, 144-165, 144-164, 145-180, 145-179, 145-178, 145-177, 145-176, 145-175, 145-174, 145-173, 145-172, 145-171, 145-170, 145-169, 145-168, 145-167, 145-166, 145-165, 146-180, 146-179, 146-178, 146-177, 146-176, 146-175, 146-174, 146-173, 146-172, 146-171, 146-170, 146-169, 146-168, 146-167, 146-166, 147-180, 147-179, 147-178, 147-177, 147-176, 147-175, 147-174, 147-173, 147-172, 147-171, 147-170, 147-169, 147-168, 147-167, 148-180, 148-179, 148-178, 148-177, 148-176, 148-175, 148-174, 148-173, 148-172, 148-171, 148-170, 148-169, 148-168, 149-180, 149-179, 149-178, 149-177, 149-176, 149-175, 149-174, 149-173, 149-172, 149-171, 149-170, 149-169, 150-180, 150-179, 150-178, 150-177, 150-176, 150-175, 150-174, 150-173, 150-172, 150-171, 150-170, 151-180, 151-179, 151-178, 151-177, 151-176, 151-175, 151-174, 151-173, 151-172, 151-171, 152-180, 152-179, 152-178, 152-177, 152-176, 152-175, 152-174, 152-173, 152-172, 153-180, 153-179, 153-178, 153-177, 153-176, 153-175, 153-174, 153-173, 153-172, 154-180, 154-179, 154-178, 154-177, 154-176, 154-175, 154-174, 154-173, 154-172, 156-180, 156-179, 156-178, 156-177, 156-176, 156-175, 156-174, 156-173, 156-172, 156-180, 156-179, 156-178, 156-177, 156-176, 156-175, 156-174, 156-173, 156-172, 157-180, 157-179, 157-178, 157-177, 157-176, 157-175, 157-174, 157-173, 157-172, 158-180, 158-179, 158-178, 158-177, 158-176, 158-175, 158-174, 158-173, 158-172, 159-180, 159-179, 159-178, 159-177, 159-176, 159-175, 159-174, 159-173, 159-172, 160-180, 160-179, 160-178, 160-177, 160-176, 160-175, 160-174, 160-173, or 160-172 of the LRP1 protein.

In some embodiments, the agent binds to amino acids 151-172 of the LRP1 protein. For example, the agent may bind to amino acids 151-172, 151-171, 151-170, 151-169, 151-168, 151-167, 151-166, 151-165, 151-164, 151-163, 151-162, 151-161, 151-160, 152-172, 152-171, 152-170, 152-169, 152-168, 152-167, 152-166, 152-165, 152-164, 152-163, 152-162, 152-161, 153-172, 153-171, 153-170, 153-169, 153-168, 153-167, 153-166, 153-165, 153-164, 153-163, 153-162, 154-172, 154-171, 154-170, 154-169, 154-168, 154-167, 154-166, 154-165, 154-164, 154-163, 155-172, 155-171, 155-170, 155-169, 155-168, 155-167, 155-166, 155-165, 155-164, 156-172, 156-171, 156-170, 156-169, 156-168, 156-167, 156-166, 156-165, 156-164, 157-172, 157-171, 157-170, 157-169, 157-168, 157-167, 157-166, 158-172, 158-171, 158-170, 158-169, 158-168, 158-167, 159-172, 159-171, 159-170, 159-169, 159-168, 160-172, 160-171, 160-170, 160-169, 161-172, 161-171, 161-170, 162-172, 162-171, or 163-172 of the LRP1 protein.

In some embodiments, the agent binds to amino acids 140-164 in the binding domain of the LRP1 protein. For example, the agent may bind to amino acids 140-164, 140-163, 140-162, 140-161, 140-160, 140-159, 140-158, 140-157, 140-156, 140-155, 140-154, 140-153, 140-152, 140-151, 140-150, 141-164, 141-163, 141-162, 141-161, 141-160, 141-159, 141-158, 141-157, 141-156, 141-155, 141-154, 141-153, 141-152, 141-151, 142-164, 142-163, 142-162, 142-161, 142-160, 142-159, 142-158, 142-157, 142-156, 142-155, 142-154, 142-153, 142-152, 143-164, 143-163, 143-162, 143-161, 143-160, 143-159, 143-158, 143-157, 143-156, 143-155, 143-154, 143-153, 144-164, 144-163, 144-162, 144-161, 144-160, 144-159, 144-158, 144-157, 144-156, 144-155, 144-154, 145-164, 145-163, 145-162, 145-161, 145-160, 145-159, 145-158, 145-157, 145-156, 145-155, 146-164, 146-163, 146-162, 146-161, 146-160, 146-159, 146-158, 146-157, 146-156, 147-164, 147-163, 147-162, 147-161, 147-160, 147-159, 147-158, 147-157, 148-164, 148-163, 148-162, 148-161, 148-160, 148-159, 148-158, 149-164, 149-163, 149-162, 149-161, 149-160, 149-159, 150-164, 150-163, 150-162, 150-161, 150-160, 151-164, 151-163, 151-162, 151-161, 152-164, 152-163, 152-162, 153-164, 153-163, or 154-164 of the LRP1 protein.

In some embodiments, the agent binds to amino acids 151-164 in the binding domain of the LRP1 protein. For example, the agent may bind to amino acids 151-164, 151-163, 151-162, 151-161, 151-160, 151-159, 151-158, 151-157, 151-156, 152-164, 152-163, 152-162, 152-161, 152-160, 152-159, 152-158, 152-157, 153-164, 153-163, 153-162, 153-161, 153-160, 153-159, 153-158, 154-164, 154-163, 154-162, 154-161, 154-160, 154-159, 155-164, 155-163, 155-162, 155-161, 155-160, 156-164, 156-163, 156-162, 156-161, 157-164, 157-163, 157-162, 158-164, 158-163, or 159-164 of the LRP1 protein.

In some embodiments, the agent may be a mixture of agents that bind different portions of the binding domain I (e.g., amino acids 1-172) of the LRP1 protein.

The amino acid sequences of full-length LRP1, amino acids 1-172 of LRP1, amino acids 140-164 of LRP-1, amino acids 151-172 of LRP1, and amino acids 151-164 of LRP1 are provided. The amino acid numbers provided herein are corresponding to the full-length LRP1 protein. One skilled in the art is able to ascertain the position and the amino acid sequence of the peptide that is bound by the agent described herein.

```
Full length LRP1 (SEQ ID NO: 1, sequence does not
contain the N-terminal 20 amino acid signal
sequence, which is removed after translation of
the protein)
IDAPKTCSPKQFACRDQITCISKGWRCDGERDCPDGSDEAPEICPQSKA

QRCQPNEHNCLGTELCVPMSRLCNGVQDCMDGSDEGPHCRELQGNCSRL

GCQHHCVPTLDGPTCYCNSSFQLQADGKTCKDFDECSVYGTCSQLCTNT

DGSFICGCVEGYLLQPDNRSCKAKNEPVDRPPVLLIANSQNILATYLSG

AQVSTITPTSTRQTTAMDFSYANETCWVHVGDSAAQTQLKCARMPGLKG

FVDEHTINISLSLHHVEQMAIDWLTGNFYFVDDIDDRIFVCNRNGDTCV

TLLDLELYNPKGIALDPAMGKVFFTDYGQIPKVERCDMDGQNRTKLVDS

KIVFPHGITLDLVSRLVYWADAYLDYIEVVDYEGKGRQTIIQGILIEHL

YGLTVFENYLYATNSDNANAQQKTSVIRVNRFNSTEYQVVTRVDKGGAL

HIYHQRRQPRVRSHACENDQYGKPGGCSDICLLANSHKARTCRCRSFGS

LGSDGKSCKKPEHELFLVYGKGRPGIIRGMDMGAKVPDEHMIPIENLMN

PRALDFHAETGFIYFADTTSYLIGRQKIDGTERETILKDGIHNVEGVAV

DWMGDNLYWTDDGPKKTISVARLEKAAQTRKTLIEGKMTHPRAIVVDPL

NGWMYWTDWEEDPKDSRRGRLERAWMDGSHRDIFVTSKTVLWPNGLSLD

IPAGRLYWVDAFYDRIETILLNGTDRKIVYEGPELNHAFGLCHHGNYLF

WTEYRSGSVYRLERGVGGAPPTVTLLRSERPPIFEIRMYDAQQQQVGTN

KCRVNNGGCSSLCLATPGSRQCACAEDQVLDADGVTCLANPSYVPPPQC

QPGEFACANSRCIQERWKCDGDNDCLDNSDEAPALCHQHTCPSDRFKCE

NNRCIPNRWLCDGDNDCGNSEDESNATCSARTCPPNQFSCASGRCIPIS

WTCDLDDDCGDRSDESASCAYPTCFPLTQFTCNNGRCININWRCDNDND

CGDNSDEAGCSHSCSSTQFKCNSGRCIPEHWTCDGDNDCGDYSDETHAN

CTNQATRPPGGCHTDEFQCRLDGLCIPLRWRCDGDTDCMDSSDEKSCEG

VTHVCDPSVKGFCKDSARCISKAWVCDGDNDCEDNSDEENCESLACRPP

SHPCANNTSVCLPPDKLCDGNDDCGDGSDEGELCGQCSLNNGGCSHNCS

VAPGEGIVCSCPLGMELGPDNHTCQIQSYCAKHLKCSQKCDQNKFSVKC

SCYEGWVLEPDGESCRSLDPFKPFIIFSNRHEIRRIDLHKGDYSVLVPG

LRNTIALDFHLSQSALYWTDVVEDKIYRGKLLDNGALTSFEVVIQYGLA

TPEGLAVDWIAGNIYWVESNLDQIEVAKLDGTLRTTLLAGDIEHPRAIA

LDPRDGILFWTDWDASLRPRIEAASMSGAGRRTVHRETGSGGWPNGLTV

DYLEKRILWIDARSDAIYSARYDGSGHMEVLRGHEFLSHPFAVTLYGGE

VYWTDWRTNTLAKANKWTGHNVTVVQRTNTQPFDLQVYHPSRQPMAPNP

-continued

CEANGGQGPCSHLCLINYNRTVSCACPHLMKLHKDNTTCYEFKKFLLYA

RQMEIRGVDLDAPYYNYIISFTVPDIDNVTVLDYDAREQRVYWSDVRTQ

AIKRAFINGTGVETVVSADLPNAHGLAVDWVSRNLFWTSYDTNKKQINV

ARLDGSFKNAVVQGLEQPHGLVVHPLRGKLYWTDGDNISMANMDGSNRT

LLFSGQKGPVGLAIDFPESKLYWISSGNHTINRCNLDGSGLEVIDAMRS

QLGKATLALAIMGDKLWWADQVSEKMGTCSKADGSGSVVLRNSTTLVMH

MKVYDESIQLDHKGTNPCSVNNGDCSQLCLPTSETTRSCMCTAGYSLRS

GQQACEGVGSFLLYSVHEGIRGIPLDPNDKSDALVPVSGTLSAVGIDFH

AENDTIYWVDMGLSTISRAKRDQTWERDVVTNGIGRVEGAIVDWIAGNI

YWTDQGFDVEIVARLNGSFRYVVISQGLDKPRAITVHPEKGYLFWTEWG

QYPRIERSRLDGTERVVLVNVSISWPNGISVDYQDGKLYWCDARTDKIE

RIDLETGENREVVLSSNNMDMFSVSVFEDFIYWSDRTHANGSIKRGSKD

NATDSVPLRTGIGVQLKDIKVFNRDRQKGTNVCAVANGGCQQLCLYRGR

GQRACACAHGMLAEDGASCREYAGYLLYSERTILKSIHLSDERNLNAPV

QPFEDPEHMKNVAILAFDYRAGTSPGTPNRIFFSDIHFGNIQQINDDGS

RRITIVENVGSVEGLAYHRGWDTLYWTSYTTSTITRHTVDQTRPGAFER

ETVITMSGDDHPRAFVLDECQNLMFWTNWNEQHPSIMRAALSGANVLTL

IEKDIRTPNGLAIDHRAEKLYFSDATLDKIERCEYDGSHRYVILKSEPV

HPFGLAVYGEHIFWTDWVRRAVQRANKHVGSNMKLLRVDIPQQPMGIIA

VANDTNSCELSPCRINNGGCQDLCLLTHQGHVNCSCRGGRILQDDLTCR

AVNSSRAQDEFECANGECINFSLTCDGVPHCKDKSDEKPSYCNSRRCKK

TFRQCSNGRCVSNMLWCNGADDCGDGSDEIPCNKTACGVGEFRCRDGTC

IGNSRRCNQFVDCEDASDEMNCSATDCSSYFRLGVKGVLFQPCERTSLC

YAPSWVCDGANDCGDYSDERDCPGVKRPRCPLNYFACPSGRCIPMSWTC

DKEDDCEHGEDETHCNKFCSEAQFECQNHRCISKQWLLCDGSDDCGDGS

DEAAHCEGKTCGPSSFSCPGTHVCVPERWLCDGDKDCADGADESIAAGC

LYNSTCDDREFMCQNRQCIPKHFVCDHDRDCADGSDESPECEYPTCGPS

EFRCANGRCLSSRQWECDGENDCHDQSDEAPKNPHCTSQEHKCNASSQF

LCSSGRCVAEALLCNGQDDCGDSSDERGCHINECLSRKLSGCSQDCEDL

KIGFKCRCRPGFRLKDDGRTCADVDECSTTFPCSQRCINTHGSYKCLCV

EGYAPRGGDPHSCKAVTDEEPFLIFANRYYLRKLNLDGSNYTLLKQGLN

NAVALDFDYREQMIYWTDVTTQGSMIRRMHLNGSNVQVLHRTGLSNPDG

LAVDWVGGNLYWCDKGRDTIEVSKLNGAYRTVLVSSGLREPRALVVDVQ

NGYLYWTDWGDHSLIGRIGMDGSSRSVIVDTKITWPNGLTLDYVTERIY

WADAREDYIEFASLDGSNRHVVLSQDIPHIFALTLFEDYVYWTDWETKS

INRAHKTTGTNKTLLISTLHRPMDLHVFHALRQPDVPNHPCKVNNGGCS

NLCLLSPGGGHKCACPTNFYLGSDGRTCVSNCTASQFVCKNDKCIPFWW

KCDTEDDCGDHSDEPPDCPEFKCRPGQFQCSTGICTNPAFICDGDNDCQ

DNSDEANCDIHVCLPSQFKCTNTNRCIPGIFRCNGQDNCGDEDERDCP

EVTCAPNQFQCSITKRCIPRVWVCDRDNDCVDGSDEPANCTQMTCGVDE

FRCKDSGRCIPARWKCDGEDDCGDGSDEPKEECDERTCEPYQFRCKNNR
```

```
CVPGRWQCDYDNDCGDNSDEESCTPRPCSESEFSCANGRCIAGRWKCDG

DHDCADGSDEKDCTPRCDMDQFQCKSGHVIPLRWRCDADADCMDGSDEE

ACGTGVRTCPLDEFQCNNTLCKPLAWKCDGEDDCGDNSDENPEECARFV

CPPNRPFRCKNDRVCLWIGRQCDGTDNCGDGTDEEDCEPPTAHTTHCKD

KKEFLCRNQRCLSSSLRCNMFDDCGDGSDEEDCSIDPKLTSCATNASIC

GDEARCVRTEKAAYCACRSGFHTVPGQPGCQDINECLRFGTCSQLCNNT

KGGHLCSCARNFMKTHNTCKAEGSEYQVLYIADDNEIRSLFPGHPHSAY

EQAFQGDESVRIDAMDVHVKAGRVYWTNWHTGTISYRSLPPAAPPTTSN

RHRRQIDRGVTHLNISGLKMPRGIAIDWVAGNVYWTDSGRDVIEVAQMK

GENRKTLISGMIDEPHAIVVDPLRGTMYWSDWGNHPKIETAAMDGTLRE

TLVQDNIQWPTGLAVDYHNERLYWADAKLSVIGSIRLNGTDPIVAADSK

RGLSHPFSIDVFEDYIYGVTYINNRVFKIHKFGHSPLVNLTGGLSHASD

VVLYHQHKQPEVTNPCDRKKCEWLCLLSPSGPVCTCPNGKRLDNGTCVP

VPSPTPPPDAPRPGTCNLQCFNGGSCFLNARRQPKCRCQPRYTGDKCEL

DQCWEHCRNGGTCAASPSGMPTCRCPTGFTGPKCTQQVCAGYCANNSTC

TVNQGNQPQCRCLPGFLGDRCQYRQCSGYCENFGTCQMAADGSRQCRCT

AYFEGSRCEVNKCSRCLEGACVVNKQSGDVTCNCTDGRVAPSCLTCVGH

CSNGGSCTMNSKMMPECQCPPHMTGPRCEEHVFSQQQPGHIASILIPLL

LLLLLVLVAGVVFWYKRRGQGAKGFQHQRMTNGAMNVEIGNPTYKMYEG

GEPDDVGGLLDADFALDPDKPTNFTNPVYATLYMGGHGSRHSLASTDEK

RELLGRGPEDEIGDPLA

LRP1 amino acids 1-172 (SEQ ID NO: 2)
IDAPKTCSPKQFACRDQITCISKGWRCDGERDCPDGSDEAPEICPQSKA

QRCQPNEHNCLGTELCVPMSRLCNGVQDCMDGSDEGPHCRELQGNCSRL

GCQHHCVPTLDGPTCYCNSSFQLQADGKTCKDFDECSVYGTCSQLCTNT

DGSFICGCVEGYLLQPDNRSCKAKN

LRP1 amino acids 140-164 (SEQ ID NO: 18)
YGTCSQLCTNTDGSFICGCVEGYLL

LRP1 amino acids 151-172 (SEQ ID NO: 3)
FICGCVEGYLLQPDNRSCKAKN

LRP1 amino acids 151-164 (SEQ ID NO: 19)
FICGCVEGYLL
```

In some embodiments, the agent that binds to the binding domain I of LRP1 is a protein or peptide. In some embodiments, the agent that binds to the binding domain I of LRP1 is an antibody. In some embodiments, the agent that binds to the binding domain I of LRP1 is an antibody fragment. In some embodiments, the agent that bind to binding domain I of the LRP protein (e.g., amino acids 1-172) is a small molecule. One skilled in the art is familiar with methods of identifying small molecules that bind to any protein or peptide.

The agent described herein (e.g., an antibody or a small molecule), when binds to binding domain I of the LRP1 protein (e.g., amino acids 1-172), activates a Rho-GTPase pathway. In some embodiments, the Rho-GTPase pathway is mediated by LRP-1. This is based, at least in part, on the findings of the present disclosure that a prosaposin-derived peptide activates the Rho-GTPase pathway in a LRP1-dependent manner (e.g., FIG. 8A), which in turn stimulates Tsp-1 and suppresses cancer, and that the prosaposin-derived peptide binds to LRP1 in binding domain I (e.g., FIGS. 13A and 13B).

A "Rho-GTPase" is a molecular switch that controls a wide variety of signal transduction pathways in all eukaryotic cells. Rho GTPases play important roles in regulating the actin cytoskeleton, regulating cell polarity, microtubule dynamics, membrane transport pathways, and transcription. A "Rho-GTPase pathway" refers to a signal transduction pathway that is regulated by a Rho GTPase. "Activate a Rho-GTPase pathway" means the intensity of a signaling pathway regulated by a Rho GTPase is enhanced by at least 30% (e.g., at least 30%, at least 40%, at least 50%, at least 60%, at least 70%, at least 80%, at least 90%, at least 100%, at least 2-fold, at least 3-fold, at least 5-fold, at least 10-fold, at least 20-fold, at least 50-fold, at least 100-fold, or more) after the activation, compared to before.

"Stimulate," as used herein, means to activate or to increase the level or activity of a biological molecule (e.g., a protein). For example, the agent of the present disclosure "stimulates Tsp-1" means the expression level or activity level of Tsp1 is increased by at least 30% (e.g., at least 30%, at least 40%, at least 50%, at least 60%, at least 70%, at least 80%, at least 90%, at least 100%, at least 2-fold, at least 3-fold, at least 5-fold, at least 10-fold, at least 20-fold, at least 50-fold, at least 100-fold, or more) in the presence of the agent, as compared to without the agent.

Further provided herein are agents that inhibit function of PRSS2. "The function of PRSS2" refers to its protease function and any other biological function it has. Known biological function of PRSS2 include, but are not limited to: (i) upregulation in a subject with pancreatitis; (ii) activating pro-urokinase in ovarian tumors; (iii) cleaving type II collagen triple helix in rheumatoid arthritis synovitis tissue; and (iv) degrading type II collagen-rich cartilage matrix. It is described herein that PRSS2 binds to LRP1 and represses Tsp-1.

In some embodiments, the agent may inhibit the ability of PRSS2 to repress Tsp-1. In some embodiments, the agent inhibits the expression of PRSS2. In some embodiments, the agent inhibits the binding of PRSS2 to LRP1 (e.g., to binding domain I of LRP1). In some embodiments, the agent does not inhibit the enzymatic activity (protease activity) of PRSS2.

"Inhibit," as used herein, means to prevent expression, to reduce the level of a protein PRSS2), or to decrease the activity of a biological molecule (e.g., a protein). For example, an agent that inhibits the expression of PRSS2 may prevent PRSS2 from being expressed, or it may reduce the level of PRSS2 by at least 30% (e.g., by at least 30%, at least 40%, at least 50%, at least 60%, at least 70%, at least 80%, at least 90%, at least 95%, at least 99%, or more), compared to in the absence of the agent. An agent that inhibits the binding of PRSS2 to LRP1 may reduce the amount of PRSS2 that binds to LRP1 by (e.g., by at least 30%, at least 40%, at least 50%, at least 60%, at least 70%, at least 80%, at least 90%, at least 95%, at least 99%, or more), compared to in the absence of the agent.

Agents that inhibit the expression of a protein is known in the art. For example, protein expression may be inhibited by RNA interference (RNAi). "RNA interference (RNAi) is a biological process in which RNA molecules inhibit gene expression or translation, by neutralizing targeted mRNA molecules. In some embodiments, the agent is a microRNA, a small interfering RNA (siRNA), or a short hairpin RNA (shRNA) that inhibits the expression of PRSS2. A "microRNA" is a small non-coding RNA molecule (containing about 22 nucleotides) that functions in RNA silencing and post-transcriptional regulation of gene expression. A "siRNA" is a commonly used RNA interference (RNAi) tool for inducing short-term silencing of protein coding genes. siRNA is a synthetic RNA duplex designed to specifically target a particular mRNA for degradation. A "shRNA" an artificial RNA molecule with a tight hairpin turn that can be used to silence target gene expression via RNA interference (RNAi). Expression of shRNA in cells is typically accomplished by delivery of plasmids or through viral or bacterial vectors. In some embodiments, the shRNA that inhibits the expression of PRSS2 comprises the nucleotide sequence of CCGGTCTGAGTTCTGGTGCCGAC-TACTCGAGTAGTCGGCACCAGAACTCAGATTTT TG (SEQ ID NO: 4). The exemplary shRNA sequence is not meant to be limiting. One skilled in the art is familiar with methods of gene silencing using any of the RNA molecules described herein.

In some embodiments, the agent inhibits binding of PRSS2 to LRP1. In some embodiments, inhibiting binding of PRSS2 to LRP1 inhibits the repression of Tsp-1 by PRSS2. "Inhibits the repression of Tsp-1" means that the agent reduces the repression of PRSS2 on Tsp-1 expression or activity by at least 30% (e.g., by at least 30%, at least 40%, at least 50%, at least 60%, at least 70%, at least 80%, at least 90%, at least 95%, at least 99%, or more), compared to in the absence of the agent.

In some embodiments, an agent that inhibits binding of PRSS2 to LRP1 is a protein or a peptide that binds to PRSS2. In some embodiments, the protein or peptide is derived from binding domain I of LRP1 (e.g., amino acids 1-172 of LRP1). For example, the protein or peptide that inhibits binding of PRSS2 to LRP1 may comprise an amino acid sequence that is at least 80% identical to the amino acid sequence corresponding to amino acids 1-200, 1-199, 1-198, 1-197, 1-196, 1-195, 1-194, 1-193, 1-192, 1-191, 1-190, 1-189, 1-188, 1-187, 1-186, 1-185, 1-184, 1-183, 1-182, 1-181, 1-180, 1-179, 1-178, 1-177, 1-176, 1-175, 1-174, 1-173, 1-172, 1-171, 1-170, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, or 1-230 of the LRP1 protein. In some embodiments, the protein or peptide that inhibits binding of PRSS2 to LRP1 may comprise an amino acid sequence that is at least 80%, at least 85%, at least 90%, at least 95%, at least 99% or more identical to amino acid sequence corresponding to amino acids 1-200, 1-199, 1-198, 1-197, 1-196, 1-195, 1-194, 1-193, 1-192, 1-191, 1-190, 1-189, 1-188, 1-187, 1-186, 1-185, 1-184, 1-183, 1-182, 1-181, 1-180, 1-179, 1-178, 1-177, 1-176, 1-175, 1-174, 1-173, 1-172, 1-171, 1-170, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, or 1-230 of the LRP1 protein.

In some embodiments, the protein or peptide that inhibits binding of PRSS2 to LRP1 comprises an amino acid sequence that is at least 80% (e.g., at least 80%, at least 90%, or 100%) identical to the amino acid sequence corresponding to about amino acids 140-180 of the LRP1 protein. For example, the protein or peptide that inhibits binding of PRSS2 to LRP1 may comprise an amino acid sequence that is at least 80% (e.g., at least 80%, at least 90%, or 100%) identical to the amino acid sequence corresponding to amino acids 140-180, 140-179, 140-178, 140-177, 140-176, 140-175, 140-174, 140-173, 140-172, 140-171, 140-170, 140-169, 140-168, 140-167, 140-166, 140-165, 141-180, 141-179, 141-178, 141-177, 141-176, 141-175, 141-174, 141-173, 141-172, 141-171, 141-170, 141-169, 141-168, 141-167, 141-166, 142-180, 142-179, 142-178, 142-177, 142-176, 142-175, 142-174, 142-173, 142-172, 142-171, 142-170, 142-169, 142-168, 142-167, 143-180, 143-179, 143-178, 143-177, 143-176, 143-175, 143-174, 143-173, 143-172, 143-171, 143-170, 143-169, 143-168, 144-180, 144-179, 144-178, 144-177, 144-176, 144-175, 144-174, 144-173, 144-172, 144-171, 144-170, 144-169, 145-180, 145-179, 145-178, 145-177, 145-176, 145-175, 145-174, 145-173, 145-172, 145-171, 145-170, 146-180, 146-179, 146-178, 146-177, 146-176, 146-175, 146-174, 146-173, 146-172, 146-171, 147-180, 147-179, 147-178, 147-177, 147-176, 147-175, 147-174, 147-173, 147-172, 148-180, 148-179, 148-178, 148-177, 148-176, 148-175, 148-174, 148-173, 149-180, 149-179, 149-178, 149-177, 149-176, 149-175, 149-174, 149-173, 149-172, 151-180, 151-179, 151-178, 151-177, 151-176, 151-175, 151-174, 151-173, 151-172, 152-180, 152-179, 152-178, 152-177, 152-176, 152-175, 152-174, 152-173, 152-172, 153-180, 153-179, 153-178, 153-177, 153-176, 153-175, 153-174, 153-173, 153-172, 154-180, 154-179, 154-178, 154-177, 154-176, 154-175, 154-174, 154-173, 154-172, 156-180, 156-179, 156-178, 156-177, 156-176, 156-175, 156-174, 156-173, 156-172, 156-180, 156-179, 156-178, 156-177, 156-176, 156-175, 156-174, 156-173, 156-172, 157-180, 157-179, 157-178, 157-177, 157-176, 157-175, 157-174, 157-173, 157-172, 158-180, 158-179, 158-178, 158-177, 158-176, 158-175, 158-174, 158-173, 158-172, 159-180, 159-179, 159-178, 159-177, 159-176, 159-175, 159-174, 159-173, 159-172, 160-180, 160-179, 160-178, 160-177, 160-176, 160-175, 160-174, 160-173, or 160-172 of the LRP1 protein. In some embodiments, the protein or peptide that inhibits binding of PRSS2 to LRP1 comprises an amino acid sequence that is at least 80% (e.g., at least 80%, at least 90%, or 100%) identical to the amino acid sequence corresponding to amino acids 151-172 of the LRP1 protein (SEQ ID NO: 3). In some embodiments, the protein or peptide that inhibits binding of PRSS2 to LRP1 comprises an amino acid sequence that is at least 80% (e.g., at least 80%, at least 90%, or 100%) identical to the amino acid sequence corresponding to amino acids 140-164 of the LRP1 protein (SEQ ID NO: 18). In some embodiments, the protein or peptide that inhibits binding of PRSS2 to LRP1 comprises an amino acid sequence that is at least 80% (e.g., at least 80%, at least 90%, or 100%) identical to the amino acid sequence corresponding to amino acids 151-164 of the LRP1 protein (SEQ ID NO: 19).

In some embodiments, the protein or peptide that inhibits binding of PRSS2 to LRP1 is an antibody or an antibody fragment. In some embodiments, the antibody is a monoclonal antibody. In some embodiments, the antibody is a polyclonal antibody. In some embodiments, the antibody binds to a region of PRSS2 where PRSS2 binds LRP-1. In some embodiments, the agent that inhibits PRSS2 function is a small molecule.

The term "bind" refers to the association of two entities (e.g., two proteins). Two entities (e.g., two proteins) are considered to bind to each other when the affinity (KD) between them is $<10^{-4}$ M, $<10^{-5}$ M, $<10^{-6}$ M, $<10^{-7}$ M, $<10^{-8}$ M, $<10^{-9}$ M, $<10^{-10}$ M, $<10^{-11}$ M, or $<10^{-12}$ M. One skilled in the art is familiar with how to assess the affinity of two entities (e.g., two proteins).

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

A peptide that is "derived from" a protein (e.g., a peptide derived from binding domain I of LRP1) means the peptide is obtained from the protein and has an amino acid sequence that shares homology with the fragment of the protein it corresponds to. The amino acid sequence of the peptide may be at least 70%, at least 75%, at least 80%, at least 85%, at least 90%, at least 95%, at least 99% or 100% identical to the amino acid sequence of the fragment of the protein it corresponds to. A peptide that is derived from a protein may also contain chemical modifications, amino acid substitutions, and/or unnatural amino acids.

An "antibody" or "immunoglobulin (Ig)" is a large, Y-shaped protein produced mainly by plasma cells that is used by the immune system to neutralize an exogenous substance (e.g., a pathogens such as bacteria and viruses). Antibodies are classified as IgA, IgD, IgE, IgG, and IgM. "Antibodies" and "antibody fragments" include whole antibodies and any antigen binding fragment (i.e., "antigen-binding portion") or single chain thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An antibody may be a polyclonal antibody or a monoclonal antibody.

The basic 4-chain antibody unit is a heterotetrameric glycoprotein composed of two identical L chains and two H chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, (e.g., Basic and Clinical Immunology, 8th edition, Daniel P. Stites, Abba I. Terr and Tristram G. Parslow (eds.), Appleton & Lange, Norwalk, Conn., 1994, page 71 and Chapter 6, incorporated herein by reference).

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ and μ, respectively. The γ and α classes are further divided into subclasses on the basis of relatively is minor differences in CH sequence and function, e.g., humans express the following subclasses: IgG1, IgG2, IgG3, IgG4, IgA1, and IgA2.

The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see, e.g., Kabat et al., Sequences of Proteins of Immunological Interest, 5th Ed. Public Health Service, National Institutes of Health, Bethesda, Md. (1991), incorporated herein by reference). The constant domains are not involved directly in binding an antibody to an antigen, but exhibit various effector functions, such as participation of the antibody in antibody dependent cellular cytotoxicity (ADCC).

An "antibody fragment" for use in accordance with the present disclosure contains the antigen-binding portion of an antibody. The antigen-binding portion of an antibody refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (e.g., as described in Ward et al., (1989) Nature 341:544-546, incorporated herein by reference), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al, (1988) Proc. Natl. Acad. Sci. USA 85:5879-5883, incorporated herein by reference). Such single chain antibodies are also intended to be encompassed within the term "antigen-binding portion" of an antibody. These antibody fragments are obtained using conventional techniques known to those with skill in the art, and the fragments are screened for utility in the same manner as are full-length antibodies.

In some embodiments, an antibody fragment may be a Fc fragment, a Fv fragment, or a single-change Fv fragment. The Fc fragment comprises the carboxy-terminal portions of both H chains held together by disulfides. The effector functions of antibodies are determined by sequences in the Fc region, which region is also the part recognized by Fc receptors (FcR) found on certain types of cells.

The Fv fragment is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

Single-chain Fv also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding (e.g., as described in Pluckthun in The Pharmacology of Monoclonal Antibodies, vol. 113, Rosenburg and Moore eds., Springer-Verlag, New York, pp. 269-315 (1994); Borrebaeck 1995, incorporated herein by reference).

Antibodies may be isolated. An isolated antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

In some embodiments, the antibody of the present disclosure is a monoclonal antibody. A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). Monoclonal antibodies may also be isolated from phage antibody libraries, e.g., using the techniques described in Clackson et al., Nature, 352:624-628 (1991) and Marks et al., J. Mol. Biol., 222: 581-597 (1991), incorporated herein by reference.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567 and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc.), and human constant region sequences.

In some embodiments, the antibody of the present disclosure is a polyclonal antibody. A "polyclonal antibody" a mixture of different antibody molecules which react with more than one immunogenic determinant of an antigen. Polyclonal antibodies may be isolated or purified from mammalian blood, secretions, or other fluids, or from eggs. Polyclonal antibodies may also be recombinant. A recombinant polyclonal antibody is a polyclonal antibody generated by the use of recombinant technologies. Recombinantly generated polyclonal antibodies usually contain a high concentration of different antibody molecules, all or a majority of (e.g., more than 80%, more than 85%, more than 90%, more than 95%, more than 99%, or more) which are displaying a desired binding activity towards an antigen composed of more than one epitope.

Methods of producing antibodies (e.g., monoclonal antibodies or polyclonal antibodies) are known in the art. For example, a polyclonal antibody may be prepared by immunizing an animal, preferably a mammal, with an allergen of choice followed by the isolation of antibody-producing B-lymphocytes from blood, bone marrow, lymph nodes, or spleen. Alternatively, antibody-producing cells may be isolated from an animal and exposed to an allergen in vitro against which antibodies are to be raised. The antibody-producing cells may then be cultured to obtain a population of antibody-producing cells, optionally after fusion to an immortalized cell line such as a myeloma. In some embodiments, as a starting material B-lymphocytes may be isolated from the tissue of an allergic patient, in order to generate fully human polyclonal antibodies. Antibodies may be produced in mice, rats, pigs (swine), sheep, bovine material, or other animals transgenic for the human immunoglobulin genes, as starting material in order to generate fully human polyclonal antibodies. In some embodiments, mice or other animals transgenic for the human immunoglobulin genes (e.g. as disclosed in U.S. Pat. No. 5,939,598), the animals may be immunized to stimulate the in vivo generation of specific antibodies and antibody producing cells before preparation of the polyclonal antibodies from the animal by extraction of B lymphocytes or purification of polyclonal serum.

Monoclonal antibodies are typically made by cell culture that involves fusing myeloma cells with mouse spleen cells immunized with the desired antigen (i.e., hybridoma technology). The mixture of cells is diluted and clones are grown from single parent cells on microtitre wells. The antibodies secreted by the different clones are then assayed for their ability to bind to the antigen (with a test such as ELISA or Antigen Microarray Assay) or immuno-dot blot. The most productive and stable clone is then selected for future use.

In some embodiments, the antibodies described herein are "humanized" for use in human (e.g., as therapeutics). "Humanized" forms of non-human (e.g., rodent) antibodies are chimeric antibodies that contain minimal sequence derived from the non-human antibody. Humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986) Riechmann et al., Nature 332:323-329 (1988); and Presta, Curr. Op. Struct. Biol. 2:593-596 (1992).

A "small molecule," as used herein, refers to a molecule of low molecular weight (e.g., <900 daltons) organic or inorganic compound that may function in regulating a biological process. Nonlimiting examples of a small molecule include lipids, monosaccharides, second messengers, other natural products and metabolites, as well as drugs and other xenobiotics.

A "lipid" refers to a group of naturally occurring molecules that include fats, waxes, sterols, fat-soluble vitamins (such as vitamins A, D, E, and K), monoglycerides, diglycerides, triglycerides, phospholipids, and others. A "monosaccharide" refers to a class of sugars (e.g., glucose) that cannot be hydrolyzed to give a simpler sugar. Non-limiting examples of monosaccharides include glucose (dextrose), fructose (levulose) and galactose. A "second messenger" is a molecule that relay signals received at receptors on the cell surface (e.g., from protein hormones, growth factors, etc.) to target molecules in the cytosol and/or nucleus. Nonlimiting examples of second messenger molecules include cyclic AMP, cyclic GMP, inositol trisphosphate, diacylglycerol, and calcium. A "metabolite" is an molecule that forms as an intermediate produce of metabolism. Non-limiting examples of a metabolite include ethanol, glutamic acid, aspartic acid, 5' guanylic acid, Isoascorbic acid, acetic acid, lactic acid, glycerol, and vitamin B2. A "xenobiotic" is a foreign chemical substance found within an organism that is not normally naturally produced by or expected to be present within. Non-limiting examples of xenobiotics include drugs, antibiotics, carcinogens, environmental pollutants, food additives, hydrocarbons, and pesticides.

The agent (e.g., an agent that binds to binding domain I of LRP-1 and/or stimulates Tsp-1 or an agent that inhibits the ability of PRSS2 to inhibit Tsp-1) may be formulated in a pharmaceutical composition. In some embodiments, the pharmaceutical composition further comprises a pharmaceutical acceptable carrier. The term "pharmaceutically-acceptable carrier" as used herein means one or more compatible solid or liquid filler, diluents or encapsulating substances which are suitable for administration into a subject, e.g., a human. A pharmaceutically acceptable carrier is "acceptable" in the sense of being compatible with the other ingredients of the formulation and not injurious to the tissue of the patient (e.g., physiologically compatible, sterile, physiologic pH, etc.). The term "carrier" denotes an organic or inorganic ingredient, natural or synthetic, with which the active ingredient is combined to facilitate the application. The components of the pharmaceutical compositions also are capable of being co-mingled with the molecules of the present disclosure, and with each other, in a manner such that there is no interaction which would substantially impair the desired pharmaceutical efficacy. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium laurel sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation.

The pharmaceutical compositions may conveniently be presented in unit dosage form and may be prepared by any of the methods well-known in the art of pharmacy. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

The formulation of the pharmaceutical composition may dependent upon the route of administration. Injectable preparations suitable for parenteral administration or intratumoral, peritumoral, intralesional or perilesional administration include, for example, sterile injectable aqueous or oleaginous suspensions and may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3 propanediol or 1,3 butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

For topical administration, the pharmaceutical composition can be formulated into ointments, salves, gels, or creams, as is generally known in the art. Topical administration can utilize transdermal delivery systems well known in the art. An example is a dermal patch.

Compositions suitable for oral administration may be presented as discrete units, such as capsules, tablets, lozenges, each containing a predetermined amount of the anti-inflammatory agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In some embodiments, the pharmaceutical compositions used for therapeutic administration must be sterile. Sterility is readily accomplished by filtration through sterile filtration membranes (e.g., 0.2 micron membranes). Alternatively, preservatives can be used to prevent the growth or action of microorganisms. Various preservatives are well known and include, for example, phenol and ascorbic acid. The cyclic Psap peptide and/or the pharmaceutical composition ordinarily will be stored in lyophilized form or as an aqueous solution if it is highly stable to thermal and oxidative denaturation. The pH of the preparations typically will be about from 6 to 8, although higher or lower pH values can also be appropriate in certain instances.

Other aspects of the present disclosure provide methods of treating cancer, using the agents and pharmaceutical compositions described herein. In some embodiments, the method comprises administering to a subject in need thereof an effective amount of an agent that stimulates Tsp-1. In some embodiments, the method comprises administering to the subject in need there of an agent that binds to binding domain I of LRP-1 as described herein (e.g., an antibody that targets amino acids 151-172 of LRP1). In some embodiments, the method comprises administering to the subject in need there of an agent that inhibits the ability of PRSS2 to repress Tsp-1. In some embodiments, the method comprising administering to the subject in need thereof an effective amount of a first agent that inhibits the PRSS2 (e.g., the ability of PRSS2 to repress Tsp-1), and an effective amount of a second agent that binds to binding domain I of LRP1. When more than one agent is administered, they may be administered simultaneously or sequentially. One skilled in the art (e.g., a physician) is able to determine the mode of administration.

"Treat" or "treatment" of cancer includes, but is not limited to, preventing, reducing, or halting the development of a cancer, reducing or eliminating the symptoms of cancer, suppressing or inhibiting the growth of a cancer, preventing or reducing metastasis and/or invasion of an existing cancer, promoting or inducing regression of the cancer, inhibiting or suppressing the proliferation of cancerous cells, reducing angiogenesis and/or increasing the amount of apoptotic cancer cells.

An "effective amount" is a dosage of an agent sufficient to provide a medically desirable result, such as treatment of cancer. The effective amount will vary with the particular disease or disorder being treated, the age and physical condition of the subject being treated, the severity of the condition, the duration of the treatment, the nature of any concurrent therapy, the specific route of administration and the like factors within the knowledge and expertise of the health practitioner. For administration to a subject such as a human, a dosage of from about 0.001, 0.01, 0.1, or 1 mg/kg up to 50, 100, 150, or 500 mg/kg or more can typically be employed.

In some embodiments, the effective amount is a dosage of an agent that causes no toxicity to the subject. In some embodiments, the effective amount is a dosage of an agent that causes reduced toxicity to the subject. Methods for measuring toxicity are well known in the art (e.g., biopsy/histology of the liver, spleen, and/or kidney; alanine transferase, alkaline phosphatase and bilirubin assays for liver toxicity; and creatinine levels for kidney toxicity).

The agents and pharmaceutical compositions described herein can be formulated for a variety of modes of administration, including systemic, topical or localized administration. A variety of administration routes are available. The particular mode selected will depend upon the type of cancer being treated and the dosage required for therapeutic efficacy. The methods of the disclosure, generally speaking, may be practiced using any mode of administration that is medically acceptable, meaning any mode that produces effective levels of the active compounds without causing clinically unacceptable adverse effects. Such modes of administration include, but are not limited to, oral, rectal, topical, nasal, intradermal, or parenteral routes. The term "parenteral" includes subcutaneous, intravenous, intramuscular, or infusion. The pharmaceutical compositions described herein are also suitably administered by intratumoral, peritumoral, intralesional, intratracheal, intracerebroventricular, intraperitoneal or perilesional routes, to exert local as well as systemic effects.

Techniques and formulations generally can be found in Remington: The Science and Practice of Pharmacy, Pharmaceutical Press; 22nd edition and other similar references. When administered, a Psap peptide may be applied in pharmaceutically-acceptable amounts and in pharmaceutically-acceptable compositions. Pharmaceutical compositions and pharmaceutically-acceptable carriers are also described herein. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the disclosure. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

In some embodiments, treatment of cancer with the agents or pharmaceutical compositions described may be combined with another therapy, such as a chemotherapy agent, radiation, a cytostatic agent, an anti-VEGF agent, an anti-angiogenesis factor, a p53 reactivation agent and/or surgery.

A subject shall mean a human or vertebrate animal or mammal including but not limited to a rodent, e.g., a rat or a mouse, dog, cat, horse, cow, pig, sheep, goat, turkey, chicken, and primate, e.g., monkey. The methods of the present disclosure are useful for treating a subject in need thereof. A subject in need thereof can be a subject who has a risk of developing cancer (i.e., via a genetic test) or a subject who has cancer.

Subjects having cancer may be identified using any method known in the art (e.g., blood tests, histology, CT scan, X-ray, MRI, physical exam, cytogenitic analysis, urinalysis, or genetic testing). A subject suspected of having cancer might show one or more symptoms of the disease. Signs and symptoms for cancer are well known to those of ordinary skill in the art. Some exemplary laboratory tests include, but are not limited to, testing for cancer biomarkers such as cancer antigen (CA) 15-3, carcinoembryonic antigen (CEA) and HER-2 for breast cancer, human papillomavirus (HPV) E6 and E7 oncoproteins for cervical cancer, alpha-fetoprotein (AFP), AFP fractions L3, P4/5, and the +II band, and ultrasonography for hepatocellular carcinoma (HCC), prostate-specific antigen (PSA) for prostate cancer, and serum CA-125 for ovarian and HCC.

The cancer can be benign or malignant, and it may or may not have metastasized. Any type of cancer is contemplated herein, including, but not limited to, leukemias, lymphomas, myelomas, carcinomas, metastatic carcinomas, sarcomas, adenomas, nervous system cancers and genitourinary cancers. Exemplary cancer types include, but are not limited to, adult and pediatric acute lymphoblastic leukemia, acute myeloid leukemia, adrenocortical carcinoma, AIDS-related cancers, anal cancer, cancer of the appendix, astrocytoma basal cell carcinoma, bile duct cancer, bladder cancer, bone cancer, biliary tract cancer, osteosarcoma, fibrous histiocytoma, brain cancer, brain stem glioma, cerebellar astrocytoma, malignant glioma, glioblastoma, ependymoma, medulloblastoma, supratentorial primitive neuroectodermal tumors, hypothalamic glioma, breast cancer, male breast cancer, bronchial adenomas, Burkitt lymphoma, carcinoid tumor, carcinoma of unknown origin, central nervous system lymphoma, cerebellar astrocytoma, malignant glioma, cervical cancer, childhood cancers, chronic lymphocytic leukemia, chronic myelogenous leukemia, acute lymphocytic and myelogenous leukemia, chronic myeloproliferative disorders, colorectal cancer, cutaneous T-cell lymphoma, endometrial cancer, ependymoma, esophageal cancer, Ewing family tumors, extracranial germ cell tumor, extragonadal germ cell tumor, extrahepatic bile duct cancer, intraocular melanoma, retinoblastoma, gallbladder cancer, gastric cancer, gastrointestinal stromal tumor, extracranial germ cell tumor, extragonadal germ cell tumor, ovarian germ cell tumor, gestational trophoblastic tumor, glioma, hairy cell leukemia, head and neck cancer, hepatocellular cancer, Hodgkin lymphoma, non-Hodgkin lymphoma, hypopharyngeal cancer, hypothalamic and visual pathway glioma, intraocular melanoma, islet cell tumors, Kaposi sarcoma, kidney cancer, renal cell cancer, laryngeal cancer, lip and oral cavity cancer, small cell lung cancer, non-small cell lung cancer, primary central nervous system lymphoma, Waldenstrom macroglobulinema, malignant fibrous histiocytoma, medulloblastoma, melanoma, Merkel cell carcinoma, malignant mesothelioma, squamous neck cancer, multiple endocrine neoplasia syndrome, multiple myeloma, mycosis fungoides, myelodysplastic syndromes, myeloproliferative disorders, chronic myeloproliferative disorders, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary cancer, plasma cell neoplasms, pleuropulmonary blastoma, prostate cancer, rectal cancer, rhabdomyosarcoma, salivary gland cancer, soft tissue sarcoma, uterine sarcoma, Sezary syndrome, non-melanoma skin cancer, small intestine cancer, squamous cell carcinoma, squamous neck cancer, supratentorial primitive neuroectodermal tumors, testicular cancer, throat cancer, thymoma and thymic carcinoma, thyroid cancer, transitional cell cancer, trophoblastic tumors, urethral cancer, uterine cancer, uterine sarcoma, vaginal cancer, vulvar cancer, choriocarcinoma, hematological neoplasm, adult T-cell leukemia, lymphoma, lymphocytic lymphoma, stromal tumors and germ cell tumors, or Wilms tumor. In some embodiments, the cancer is melanoma or ovarian cancer.

EXAMPLES

The progression of cancer to the metastatic stage is a major contributing factor to its lethality. In order for a tumor to form lethal metastases it must gain access to the vasculature or lymphatic system (intravasation), survive during transit, exit the vascular or lymphatic channels (extravasation), and proliferate at the metastatic site [1]. In this process, heterotypic signaling between the tumor and its microenvironment can affect tumor growth by regulating the production and secretion of factors that mediate tumor growth, angiogenesis, and the immune response. Two proteins, prosaposin and PRSS2, were identified through a functional proteomic screen, designed to identify secreted proteins that modulate Tsp-1 in the microenvironment [2]. Prosaposin is expressed preferentially by weakly metastatic tumors and stimulates Tsp-1 in the tumor microenvironment. Conversely, PRSS2 is preferentially expressed by highly metastatic cells and inhibits Tsp-1 expression in the tumor microenvironment. Tsp-1 inhibits tumor growth and progression via multi-modal activity, specifically: (1) It is a broadly acting anti-angiogenic factor, (2) It has direct anti-tumor activity against tumors that express CD36, and (3) It promotes macrophage phagocytosis and T-cell activation via binding to CD47 [3-5]. The Tsp-1 stimulating activity of prosaposin and the Tsp-1 repressing activity of PRSS2 have both been determined to be mediated via binding to LRP1. Provided herein are antibodies that mimic prosaposin's Tsp-1 stimulating activity and block the Tsp-1 repressing activity of PRSS2.

The current standard of care for cancer patients consists of broadly acting cytotoxic agents (chemotherapy), radiation, and directed therapeutics that target specific secreted proteins, cell surface receptors, or kinases. Historically, there have been two classes of therapeutics that target the tumor microenvironment, anti-angiogenic drugs (which have been limited to anti-VEGF therapies) and immunomodulatory drugs. One of the major drawbacks to therapies that target the microenvironment is that they do not have direct anti-tumor activity and thus their efficacy as monotherapies has been limited. Conversely, a major drawback of targeted therapies and chemotherapies that have direct anti-tumor activity is that patients develop resistance to the drug, in addition to unintended deleterious side effects. As such, a therapeutic strategy involving a combination of targeted therapies/chemotherapy and anti-angiogenic/immunomodulatory drugs has been used with the goal of first shrinking the tumor, via the activity of the anti-tumor drug and then holding the tumor at bay via the activity of the therapy targeting the tumor microenvironment. The development of antibodies that specifically target the tumor microenvironment to increase the expression of Tsp-1, a protein with potent anti-tumor, anti-angiogenic and immunomodulatory activity, would have enormous therapeutic potential.

Prosaposin was first identified as a novel suppressor of tumor metastasis, and such inhibition was documented to be achieved by stimulating p53 and subsequently Tsp-1 in the tumor microenvironment [2]. A 5-amino acid cyclic peptide from prosaposin with potent anti-tumor and anti-metastatic activity has since been identified. In Aim 1, the binding affinity and activity of the psaptide will be optimized. In Aim 2, the optimized psaptide will be developed as a therapeutic agent and tested in orthotopic xenograft, syngeneic and spontaneous genetic models of primary and metastatic cancer. In Aim 2, patient tumor tissue samples for CD36, CD47, Tsp-1 and psap expression will also be screened to expand the potential indications for the psaptide. For Aim 2, collaborations will be with the Drapkin lab at Dana Farber Cancer Institute and Harvard Medical School, as well as the Akslen Lab at the Center for Cancer Biomarkers at the University of Bergen, Norway and the Kimmelman Lab at Brigham and Women's Hospital and Harvard Medical School.

The Psaptide Inhibits Primary Pancreatic Tumor Growth and Metastasis

A 4-amino acid peptide derived from prosaposin that stimulates bone marrow-derived myeloid cells, normally recruited to stimulate tumor growth to express the potent anti-angiogenic and anti-tumorigenic protein Tsp-1, has been identified.

Figure 2A:
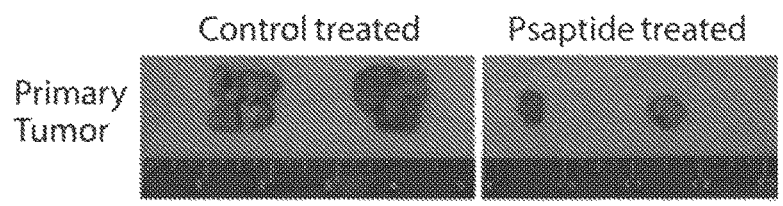
FIGS. 2A-2B. Representative images of (FIG. 2A) primary pancreatic tumors and (FIG. 2B) the lung and spleen of mice treated with psaptide or vehicle control.
Figure 2B:
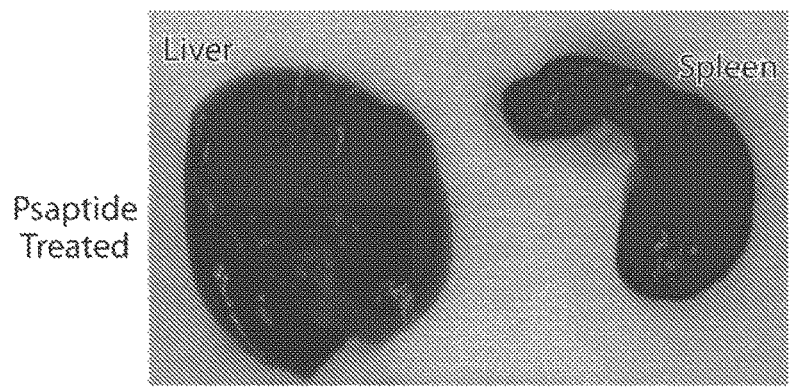
Figure 2B:
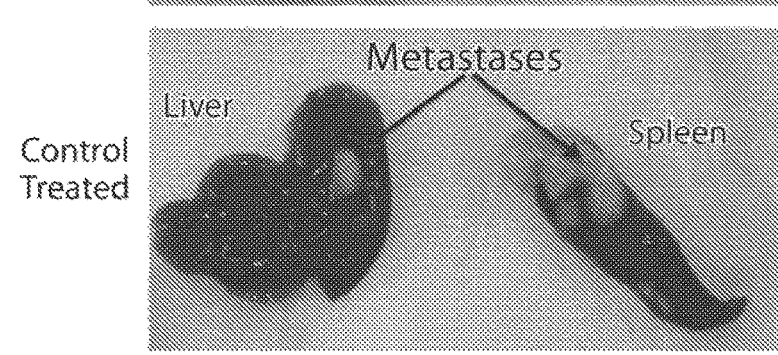

The prosaposin peptide has been shown to inhibit metastasis by stimulating Tsp-1 in bone marrow-derived cells in the tumor microenvironment [6]. As such, the hypothesis that psap would have efficacy in treating metastatic pancreatic cancer, a cancer in which the microenvironment comprises the majority of the tumor mass, was tested [7]. Accordingly, $1 \times 10^6$ AsPc1 human pancreatic cancer cells expressing firefly luciferase were injected into the pancreas of SCID mice. The tumors were allowed to grow for 25 days, at which point the luciferase intensity was greater than $1 \times 10^8$ for all tumors. Treatment was then initiated with the psaptide at doses of 20 mg/kg and 40 mg/kg QD. All mice were sacrificed after 21 days of treatment when the control (vehicle) treated mice became moribund. As demonstrated in FIGS. 1 and 2A, the psaptide was able to significantly inhibit primary tumor growth. More significantly, upon examination of the liver and spleen, the two most common sites of metastasis for this cell line and for pancreatic cancer in general, no metastases whatsoever was observed (FIG. 2B).

Multiple Human Cancer Cells Express CD36

Figure 3A:
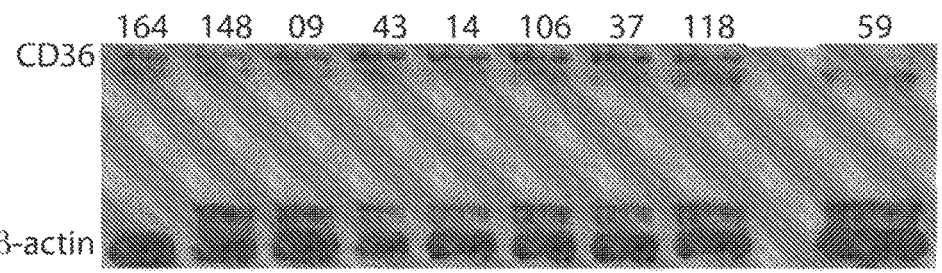
FIGS. 3A-3B. Western blot of CD36 and β-actin in (FIG. 3A) 9 ovarian cancer cell lines established from patient ascites and (FIG. 3B) breast cancer cell lines MCF7, SkBr3 and MDA-MB-231.
Figure 3B:
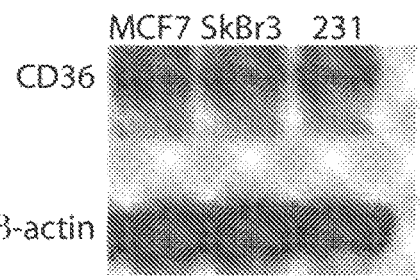

Since Tsp-1 elicits its proapoptotic activity by binding to the cell surface receptor CD36, it was examined whether human cancer cell lines express this receptor. A panel of primary human ovarian cancer cells, derived from patient ascites as well as three breast cancer cell lines representing the major subtypes ($ER^+$, $HER2^+$, and triple negative), was screened. Strikingly, all of the cells were found to express easily detectable levels of CD36 (FIGS. 3A and 3B). From this observation, it was predicted that the psaptide would have significant efficacy against ovarian cancer by inducing apoptosis in ovarian cancer cells via Tsp-1 binding to CD36, and inhibiting angiogenesis. This hypothesis will be tested in Aim 1.

Ovarian Cancer Recruit Bone Marrow Derived Myeloid Cells to Ascites that are the Target of the Peptide.

Figure 4:
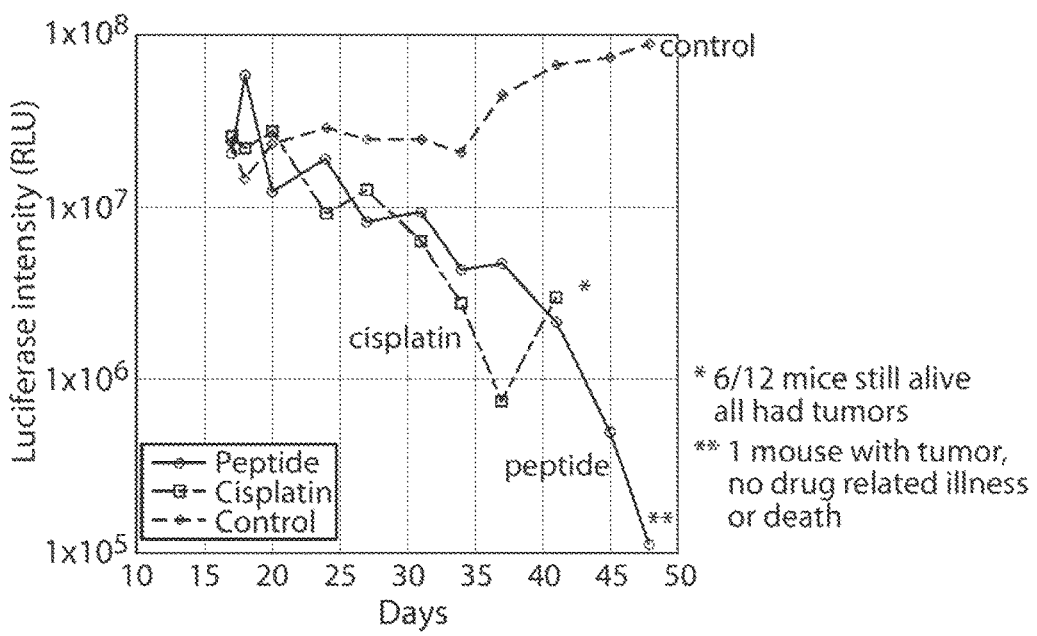
FIG. 4. SCID mice were injected with 1×10 ovarian cancer cells and treated with peptide (40 mg/kg/QD) or cisplatin (4 mg/kg QOD) (n=12/group), FIG. 5. FACS analysis of Gr1+ (x-axis) and CD11b+ (y-axis) cells in the ascites of mice that were treated with vehicle control or the peptide (psaptide).
Figure 5:
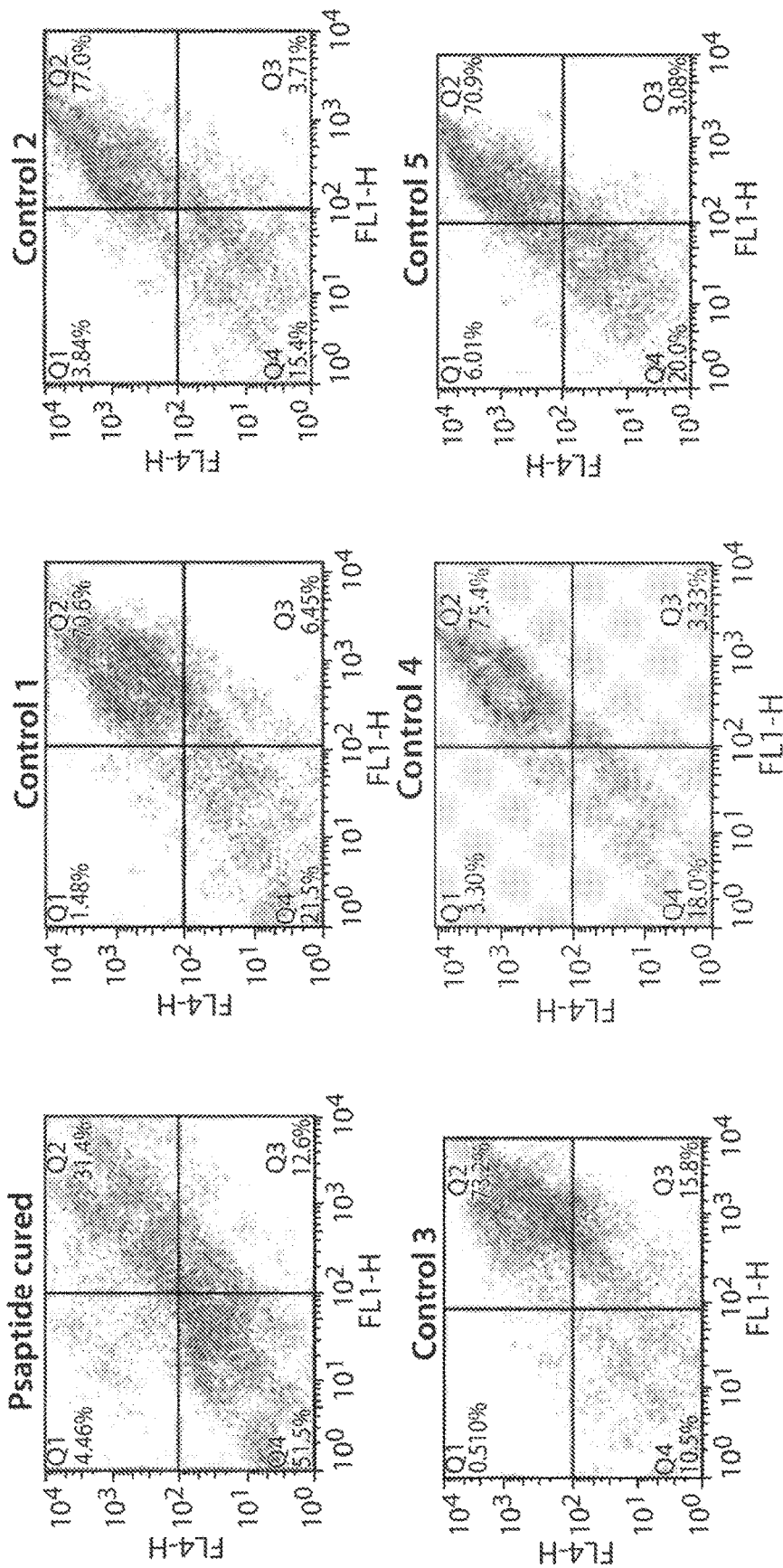

It was demonstrated that the activity of prosaposin and the therapeutic peptide are mediated by $Gr1^+/Cd11b^+$ monocytes [6]. As such, the ascites fluid from mice treated in FIG. 4 was examined for the presence of $Gr1^+/CD11b^+$ cells by FACS analysis. It was observed that the peritoneal fluid of the control-treated mice was comprised of >70% $Gr1^+/Cd11b^+$ cells, while the fluid in the peritoneal cavity mouse that had been "cured" by peptide treatment was comprised of ~30% $Gr1^+/CD11b^+$ cells (FIG. 5). This indicates that the ovarian tumor cells were recruiting these BM-derived cells.

Prosaposin Stimulation of Tsp-1 is Mediated by LRP1

It has been demonstrated that Low Density Lipoprotein Receptor Related Protein (LRP) can mediate the uptake of prosaposin [8]. Thus, in order to determine how prosaposin was able to stimulate the expression of Tsp-1 and p53 in tumor-associated fibroblasts, prostate fibroblasts were treated with PC3-conditioned media in the presence and absence of Receptor Associate Protein (RAP), a competitive inhibitor or LRP1 binding. Western blot analysis revealed that in the presence of RAP, PC3-conditioned media no longer stimulated Tsp-1 (FIGS. 6A-6B). It has also been demonstrated that ligation of LRP1 releases intracellular $Ca^{2+}$ stores [9]. To determine whether prosaposin-mediated stimulation of Tsp-1 utilized this pathway, fibroblasts were treated with CM from PC3 cells in the presence and absence of the PKC inhibitor Gö 6983. It was observed, via western blot analysis, that inhibition of PKC abolished the stimulation of Tsp-1 and p53. Thus, it is believed that Prosaposin functions via binding to LRP1.

Additionally, LRP1 expression in lung fibroblasts was knocked down with two is independent shRNA sequences and the effects on Tsp-1 expression were examined. Knocking down LRP1 was found to have no effect on Tsp-1 expression in the absence of stimulus (FIG. 7). Consistent with the results obtained from treating cells with RAP, when the lung fibroblasts were treated with conditioned media from either the weakly metastatic PC3 cell line or the metastatic PC3-LIN4 cell line, no stimulation of Tsp-1 was observed, as had been observed in cells transduced with the empty vector (FIG. 7). Strikingly, silencing LRP1 also abrogated the repression LRP1 by LN4-conditioned media, indicating that this activity was also mediated by a signaling pathway downstream from LRP1 (FIG. 7).

In order to delineate the pathway leading from LRP1 to Tsp-1 stimulation by prosaposin, two pathways that have been reported to be stimulated by LRP1 under different conditions were chosen to be examined: Rho and Rac [10]. The peptide was observed to stimulate Tsp-1 in an LRP1-dependent manner, as co-treatment with RAP blocked the stimulation of Tsp-1 in a dose-dependent fashion (FIG. 8A). Moreover, when lung fibroblasts were treated with the peptide in the presence of the Rho Kinase inhibitor Y27632, the stimulation of Tsp-1 was completely abrogated (FIG. 8B).

Figure 9:
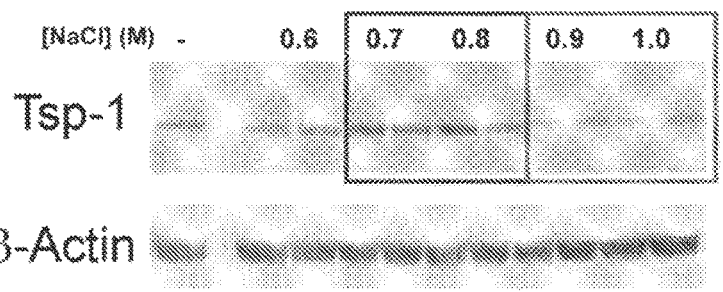
FIG. 9. Western blot analysis of Tsp-1 and β-actin expression in lung fibroblasts that were untreated (−) or treated with LN4 CM fractionated over a $Cu^{2+}$/heparin sepharose column with increasing concentrations of NaCl.
Figure 10:
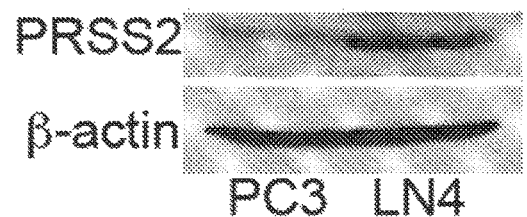
FIG. 10. Western blot analysis of PRSS2 and β-actin expression in PC3 and PC3M-LN4 cells.
Figure 11:
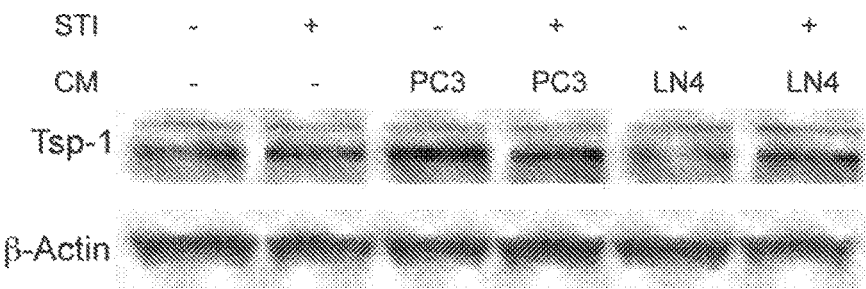
FIG. 11. Western blot analysis of Tsp-1 and β-actin expression in lung fibroblasts that were untreated (−) or treated with LN4 CM alone or in combination with STI.
Figure 12:
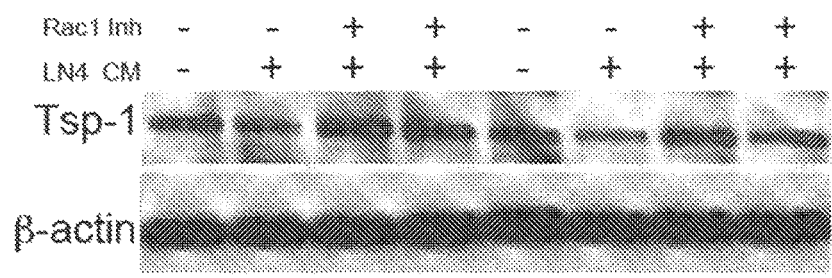
FIG. 12. Western blot analysis of Tsp-1 and β-actin expression in lung fibroblasts that is were untreated (−) or treated with LN4 CM alone or in combination with Rac1 inhibitor.

Attention was then turned to the mechanism by which PC3M-LN4 cells repress Tsp-1 in the tumor microenvironment. In doing so, LN4 conditioned media (CM) was fractionated over a $Cu^{2+}$/heparin sepharose column with increasing concentrations of NaCl. The eluted fractions were used to treat lung fibroblasts and Tsp-1 induction was analyzed by western blot. The fractions eluted between 0.9 and 1.0M NaCl were found to be able to stimulate Tsp-1 (FIG. 9). By analyzing the protein content of the eluted fractions by tandem liquid chromatography/mass spectrometry (LC/MS), a protein was identified that was present in the active fractions of LN4 CM, but not present in the adjacent fractions or the fractions eluted with the same NaCl concentrations from PC3 CM. The identified protein was the serine protease PRSS2. The LC/MS analysis was validated by performing a western blot of PRSS2 expression in PC3 and LN4 cells, which revealed that PRSS2 was expressed at significantly higher levels in LN4 cells (FIG. 10). It was then validated that PRSS2 was mediating the repression of Tsp-1 by treating lung fibroblasts with LN4 CM in the presence and absence of the serine protease inhibitor, STI, which completely abrogated the repression of Tsp-1 (FIG. 11). Finally, the signaling pathway emanating from LRP1 that was mediating the PRSS2-induced repression of Tsp-1 was sought to be delineated. It was speculated that if psap was stimulating Tsp-1 via LRP1-mediated activation of the Rho pathway, perhaps PRSS2 induced the repression of Tsp-1 via LRP1-mediated activation of the Rae pathway, since the two pathways are antagonistic. By treating WI38 cells with LN4 CM in the presence and absence of a Rac1 inhibitor, the repression of Tsp-1 was observed to be alleviated and Tsp-1 levels were restored to basal levels (FIG. 12). While STI is able to block the repression of Tsp-1 mediated by PRSS2 due to its lack of specificity for PRSS2 and its ability to inhibit all members of the trypsin family, it does not represent a viable therapeutic strategy. For the same reason, chemical compounds designed to inhibit PRSS2 would also lack specificity due to the conserved nature of the active sites of serine proteases and the trypsin family. Therefore, it is believed that an antibody designed to bind to PRSS2 which blocks its ability to repress Tsp-1 will be a potent anti-cancer therapeutic agent.

Figure 13B:
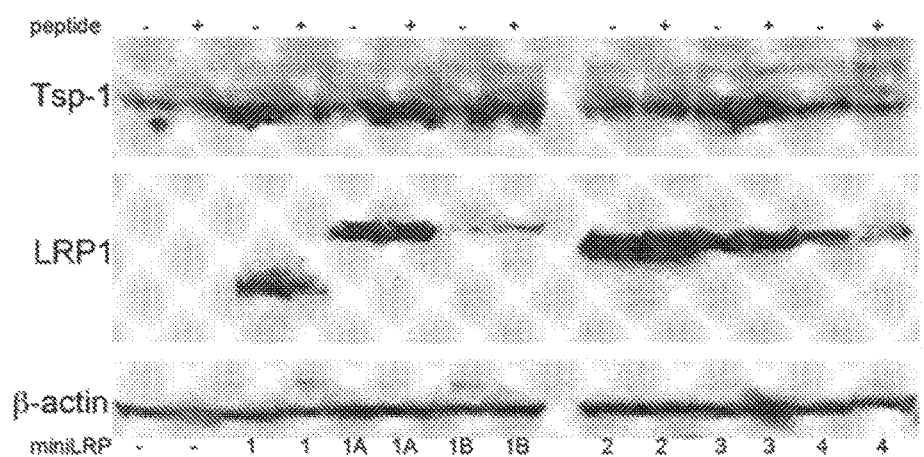
Figure 14A:
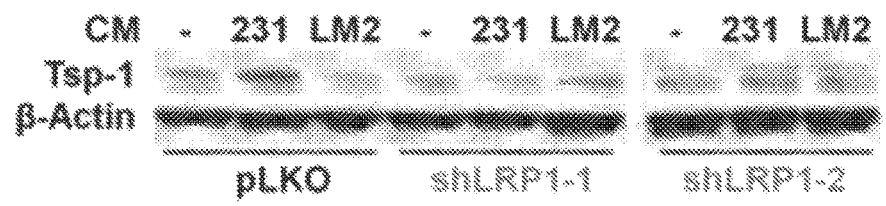
FIGS. 14A-14B. Prosaposin and PRSS2 both require LRP1 for modulation of Tsp-1 expression.
Figure 14B:
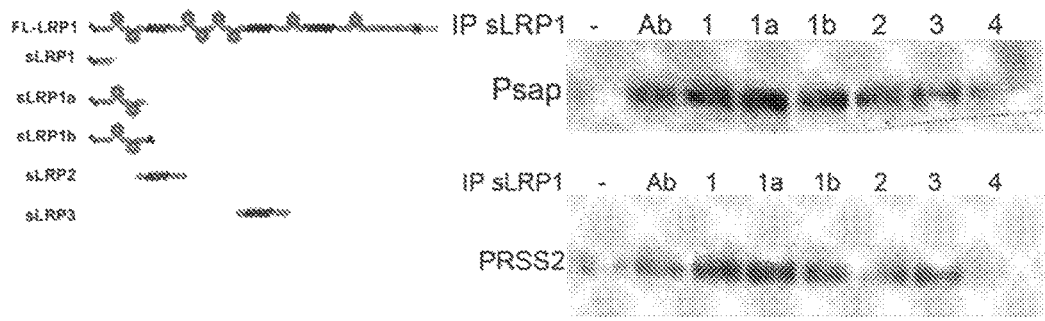
Figure 15A:
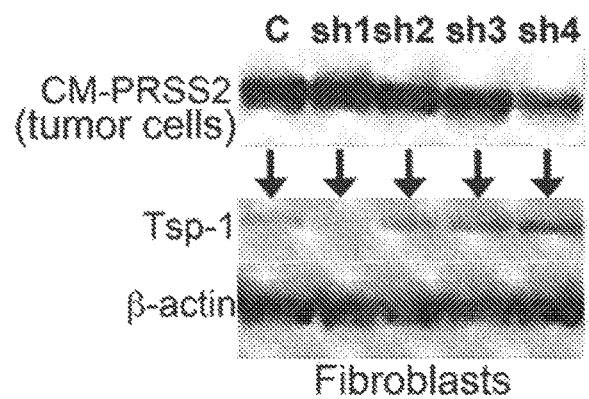
FIGS. 15A-15C. Silencing PRSS2 blocks Tsp-1 repression and tumor formation.
Figure 15B:
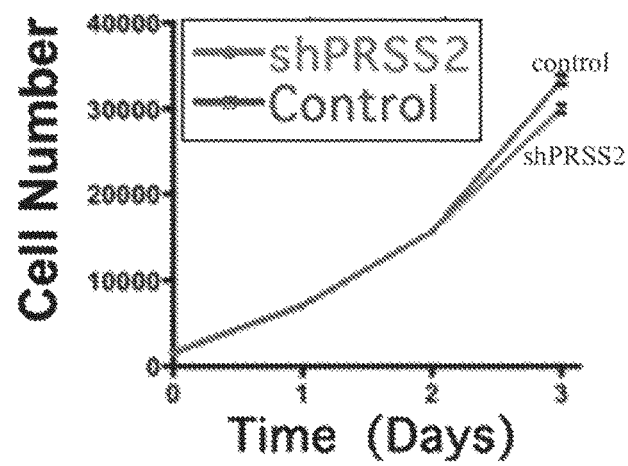
Figure 15C:
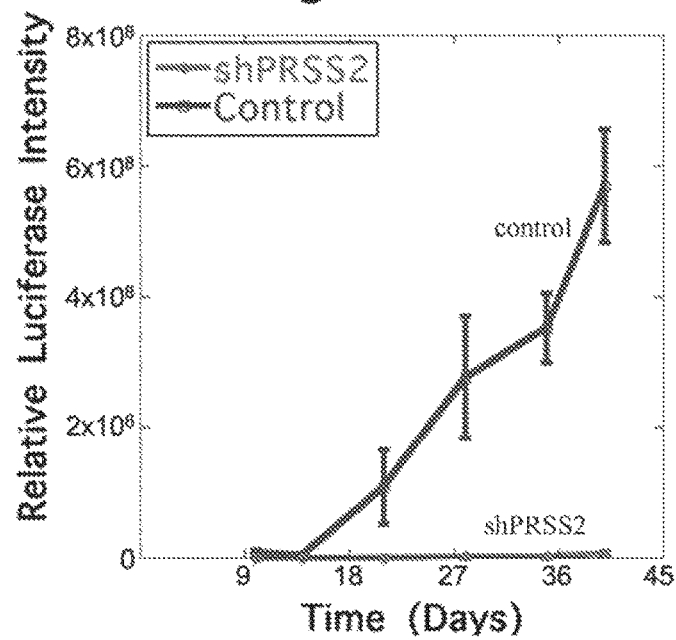

Finally, the minimal region of the LRP1 receptor that is required for the stimulation of Tsp-1 by the prosaposin peptide was sought to be determined. For these studies, mutants of LRP1 that contained different regions of the extracellular domain fused to the transmembrane and intracellular domains were utilized (FIG. 13A) [11]. 293T cells, which express very low levels of Tsp-1 and are not stimulated by the peptide to produce Tsp-1, were then transfected with these constructs (FIG. 13B). Cyclic psap peptide was found to be able to stimulate Tsp-1 in 293T cells transfected with miniLRP1a and miniLRP1b, but not in cells transfected with the other miniLRP1 constructs. Strikingly, both miniLRP1a and miniLRP1b are the only mutants that contain the N-terminus and the first two β-propeller domains. Based on these results, it is believed that prosaposin and the psap peptide stimulate Tsp-1 expression via binding to this region of LRP1. An antibody that binds to this region of LRP1 is believed to mimic the activity of the peptide and perhaps bind with even greater affinity and possess improved pharmacokinetic (PK) and pharmacodynamic (PD) properties.

LRP1 Peptides that Bind to both PSAP and PRSS2

Figure 16A:
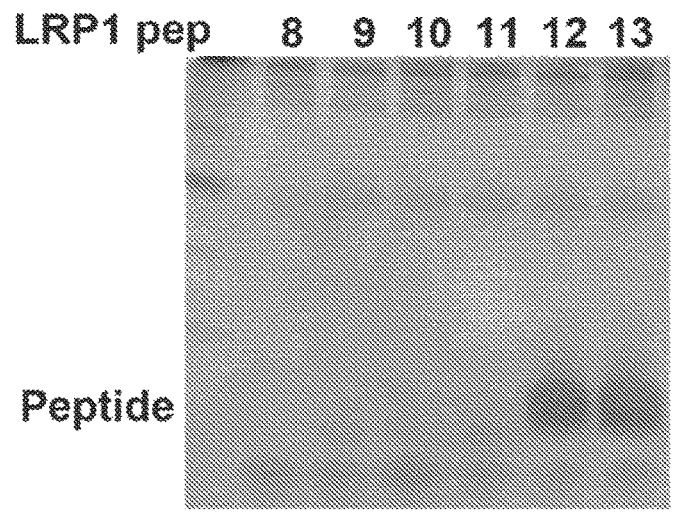
FIGS. 16A-16B. Co-immunoprecipitation of LRP1 peptides with PSAP (FIG. 16A) or PRSS2 (FIG. 16B).
Figure 16B:
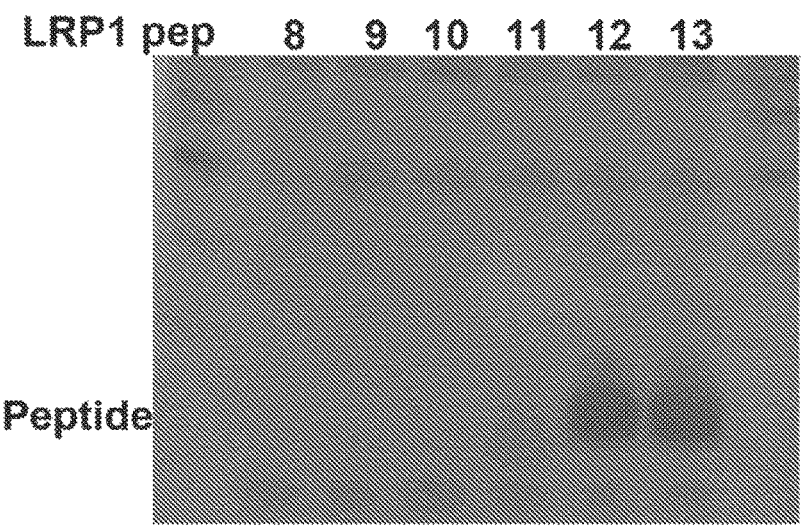

To map the binding sites on LRP1 that binds to prosaposin (PSAP) and/or PRSS2, peptides derived from binding domain I of LRP1 (SEQ ID NOs: 3 and 7-18) were tested for their ability to co-immunoprecipitate with PSAP or PRSS2. The results show that peptide 12, (corresponding to amino acids 140-164 of LRP1) and peptide 13 (corresponding to amino acids 151-172 of LRP1) bind to both PRSS2 and PSAP (FIGS. 16A-16B). Peptide 12 and peptide 13 overlap in the region corresponding to amino acids 151-164 of LRP1, indicating that the binding site of PRSS2 and PASP is within this region of LRP1.

```
shRNA sequences:
PRSS2
TRCN0000046736 (Sigma ID)
Sequence:
                                    (SEQ ID NO: 4)
CCGGTCTGAGTTCTGGTGCCGACTACTCGAGTAGTCGGCACCAGAACTCA

GATTTTTG

LRP1
1: TRCN0000257134 (Sigma ID)
Sequence:
                                    (SEQ ID NO: 5)
CCGGACAGCTTCCTGAGGGCTAATTCTCGAGAATTAGCCCTCAGGAAGCT

GTTTTTG
```

2: TRCN0000257100 (Sigma ID)
Sequence:
(SEQ ID NO: 6)
CCGGGATCCGTGTGAACCGCTTTAACTCGAGTTAAAGCGGTTCACACGGA

TCTTTTTG

LRP1 binding domain I and peptide sequences
Peptide 1 (amino acids 1-24 of LRP1):
(SEQ ID NO: 7)
IDAPKTCSPKQFACRDQITCISKGW Peptide 2 (amino acids 15-39 of LRP1):
(SEQ ID NO: 8)
RDQITCISKGWRCDGERDCPDGSDE Peptide 3 (amino acids 24-49 of LRP1):
(SEQ ID NO: 9)
RCDGERDCPDGSDEAPEICPQSKAQ Peptide 4 (amino acids 40-64 of LRP1):
(SEQ ID NO: 10)
APEICPQSKAQRCQPNENHCLGTEL Peptide 5 (amino acids 50-74 of LRP1):
(SEQ ID NO: 11)
RCQPNENHCLGTELCVPMSRLCNGV Peptide 6 (amino acids 65-89 of LRP1):
(SEQ ID NO: 12)
TELCVPMSRLCNGVQDCMDGSDEGP Peptide 7 (amino acids 75-99 of LRP1):
(SEQ ID NO: 13)
QDCMDGSDEGPHCRELQGNCSRLGC Peptide 8 (amino acids 90-114 of LRP1):
(SEQ ID NO: 14)
HCRELQGNCSRLGCQHHCVPTLDGP Peptide 9 (amino acids 100-126 of LRP1):
(SEQ ID NO: 15)
QHHCVPTLDGPTCYCNSSFQLQADGKT Peptide 10 (amino acids 115-139 of LRP1):
(SEQ ID NO: 16)
TCYCNSSFQLQADGKTCKDFDECSV Peptide 11 (amino acids 125-149 of LRP1):
(SEQ ID NO: 17)
KTCKDFDECSVYGTCSQLCTNTDGS Peptide 12 (amino acids 140-164 of LRP1, binds to both PRSS2 and prosaposin):
(SEQ ID NO: 18)
YGTCSQLCTNTDGSFICGCVEGYLL Peptide 13 (amino acids 151-172 of LRP1, binds to both PRSS2 and prosaposin):
(SEQ ID NO: 3)
FICGCVEGYLLQPDNRSCKAKN Mutations in the Active Site of PRSS2 Do Not Affect the Repression of Tsp-1

Wild-type PRSS2 in pCMVSPORT6.1 was mutated using the QuickChange mutagenesis kit: G191R, S200A, S200T and S200C (nucleotide sequences provided below). The wild-type and mutant constructs were transfected into 293T cells using FuGene transfection reagent. After 48 hours, the conditioned media containing the mutant proteins was harvested and used to treat WI-38 fibroblasts overnight. Following treatment, the cells were harvested, lysed and protein concentration determined by Bio-Rad protein assay. Equivalent levels of protein were added to each well and run on a polyacrylamide SDS gel. Western blotting with antibodies against Tsp-1 and b-actin was then performed using standard protocols.

Figure 17:
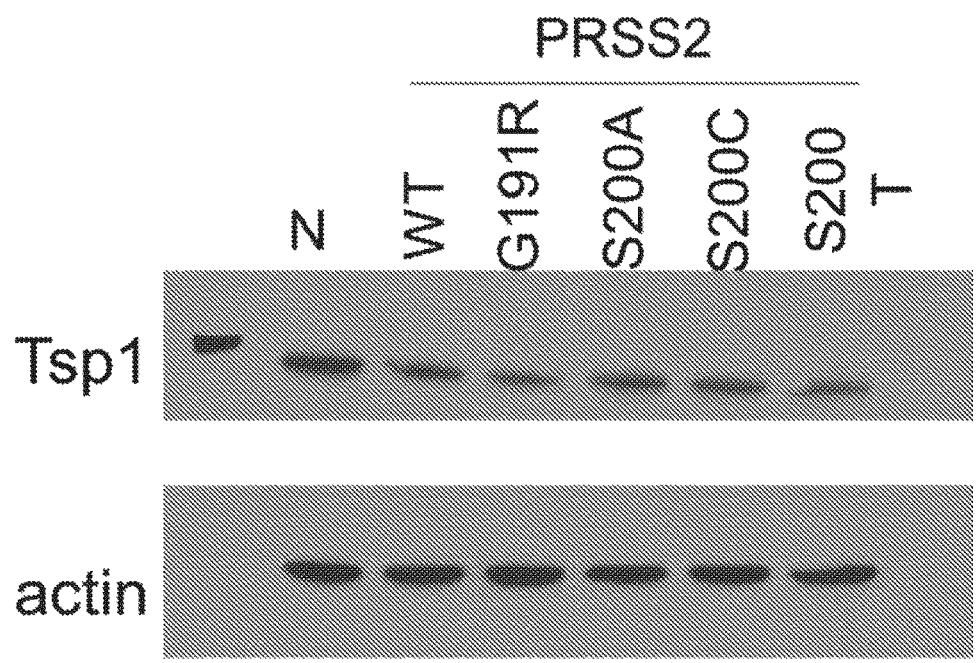
FIG. 17. Mutations in the active site of PRSS2 do not affect the repression of Tsp-1. Mutations were made in the PRSS2 active site that would abolish the enzymatic activity of PRSS2. The mutants were sequenced to confirm the presence of the mutation. The wild-type and mutant PRSS2 proteins were ectopically transfected in 293T cells and the conditioned media was used to treat WI-38 fibroblasts. Tsp-1 and β-actin expression was then analyzed by western blot. It was found that the ability of PRSS2 to repress Tsp-1 was not affected, indicating that binding site for LRP1 is not in the active site and that antibodies against this region do not affect the protease activity of the enzyme.

It was found that the ability of PRSS2 to repress Tsp-1 was not affected, indicating that binding site for LRP1 is not in the active site and that antibodies against this region do not affect the protease activity of the enzyme (FIG. 17).

PRSS2 Protein and nucleotide sequences
PRSS2 Protein (Active site: 194-205 200S, G191R inactivating mutation)
(SEQ ID NO: 19)
MNLLLILTFVAAAVAAPFDDDDKIVGGYICEENSVPYQVSLNSGYHFCGGSLISEQWVVSAGHCYKSAINSKLSGR

GCEYHRIQVRLGEHNIEVLEGNEQFINAAKIIRHPKYNSRTLDNDILLIKLSSPAVINSRVSAISLPTAPPAAGTE

SLISGWGNTLSSGADYPDELQCLDAPVLSQAECEASYPGKITNNMFCVGFLEGGK<u>DSCQGDSGGPVV</u>SNGELQGIV

SWGYGCAQKNRPGVYTKVYVYVDWIKDTIAANS

PRSS2 Nucleotide WT (Active site: 194-205 200S, G191R inactivating mutation)
(SEQ ID NO: 20)
ATGAATCTAC TTCTGATCCT TACCTTTGTT GCAGCTGCTG TTGCTGCCCC

CTTTGATGAT GATGACAAGA TCGTTGGGGG CTACATCTGT GAGGAGAATT

CTGTCCCCTA CCAGGTGTCC TTGAATTCTG GCTACCACTT CTGCGGTGGC

TCCCTCATCA GCGAACAGTG GGTGGTGTCA GCAGGTCACT GCTACAAGTC

GGCAATTAAC TCAAAATTAT CAGGAAGAGG GTGTGAATAT CACCGCATCC

AGGTGAGACT GGGAGAGCAC AACATCGAAG TCCTGGAGGG GAATGAACAG

TTCATCAATG CGGCCAAGAT CATCCGCCAC CCCAAATACA ACAGCCGGAC

TCTGGACAAT GACATCCTGC TGATCAAGCT CTCCTCACCT GCCGTCATCA

ATTCCCGCGT GTCCGCCATC TCTCTGCCCA CTGCCCCTCC AGCTGCTGGC

ACCGAGTCCC TCATCTCCGG CTGGGGCAAC ACTCTGAGTT CTGGTGCCGA

CTACCCAGAC GAGCTGCAGT GCCTGGATGC TCCTGTGCTG AGCCAGGCTG

AGTGTGAAGC CTCCTACCCT GAGAAGATTA CCAACAACAT GTTCTGTGTG

GGCTTCCTCG AGGGAGGCAA <u>GGATTCCTGC CAGGGTGATT CTGGTGGCCC</u>

<u>TGT</u>GGTCTCC AATGGAGAGC TCCAAGGAAT TGTCTCCTGG GGCTATGGCT

GTGCCCAGAA GAACAGGCCT GGAGTCTACA CCAAGGTCTA CAACTATGTG

GACTGGATTA AGGACACCAT AGCTGCCAAC AGCTAA

PRSS2 G191R Nucleotide (Active site: 194-205 200S, G191R inactivating mutation)

(SEQ ID NO: 21)

ATGAATCTAC TTCTGATCCT TACCTTTGTT GCAGCTGCTG TTGCTGCCCC

CTTTGATGAT GATGACAAGA TCGTTGGGGG CTACATCTGT GAGGAGAATT

CTGTCCCCTA CCAGGTGTCC TTGAATTCTG GCTACCACTT CTGCGGTGGC

TCCCTCATCA GCGAACAGTG GGTGGTGTCA GCAGGTCACT GCTACAAGTC

GGCAATTAAC TCAAAATTAT CAGGAAGAGG GTGTGAATAT CACCGCATCC

AGGTGAGACT GGGAGAGCAC AACATCGAAG TCCTGGAGGG GAATGAACAG

TTCATCAATG CGGCCAAGAT CATCCGCCAC CCCAAATACA ACAGCCGGAC

TCTGGACAAT GACATCCTGC TGATCAAGCT CTCCTCACCT GCCGTCATCA

ATTCCCGCGT GTCCGCCATC TCTCTGCCCA CTGCCCCTCC AGCTGCTGGC

ACCGAGTCCC TCATCTCCGG CTGGGGCAAC ACTCTGAGTT CTGGTGCCGA

CTACCCAGAC GAGCTGCAGT GCCTGGATGC TCCTGTGCTG AGCCAGGCTG

AGTGTGAAGC CTCCTACCCT GAGAAGATTA CCAACAACAT GTTCTGTGTG

GGCTTCCTCG AG<u>C</u>GAGGCAA <u>GGATTCCTGC CAGGGTGATT CTGGTGGCCC</u>

<u>TGT</u>GGTCTCC AATGGAGAGC TCCAAGGAAT TGTCTCCTGG GGCTATGGCT

GTGCCCAGAA GAACAGGCCT GGAGTCTACA CCAAGGTCTA CAACTATGTG

GACTGGATTA AGGACACCAT AGCTGCCAAC AGCTAA

PRSS2 S200A (Active site: 194-205 200A)

(SEQ ID NO: 22)

ATGAATCTAC TTCTGATCCT TACCTTTGTT GCAGCTGCTG TTGCTGCCCC

CTTTGATGAT GATGACAAGA TCGTTGGGGG CTACATCTGT GAGGAGAATT

CTGTCCCCTA CCAGGTGTCC TTGAATTCTG GCTACCACTT CTGCGGTGGC

TCCCTCATCA GCGAACAGTG GGTGGTGTCA GCAGGTCACT GCTACAAGTC

GGCAATTAAC TCAAAATTAT CAGGAAGAGG GTGTGAATAT CACCGCATCC

AGGTGAGACT GGGAGAGCAC AACATCGAAG TCCTGGAGGG GAATGAACAG

TTCATCAATG CGGCCAAGAT CATCCGCCAC CCCAAATACA ACAGCCGGAC

TCTGGACAAT GACATCCTGC TGATCAAGCT CTCCTCACCT GCCGTCATCA

ATTCCCGCGT GTCCGCCATC TCTCTGCCCA CTGCCCCTCC AGCTGCTGGC

ACCGAGTCCC TCATCTCCGG CTGGGGCAAC ACTCTGAGTT CTGGTGCCGA

CTACCCAGAC GAGCTGCAGT GCCTGGATGC TCCTGTGCTG AGCCAGGCTG

AGTGTGAAGC CTCCTACCCT GAGAAGATTA CCAACAACAT GTTCTGTGTG

GGCTTCCTCG AGGGAGGCAA <u>GGATTCCTGC CAGGGTGATG CTGGTGGCCC</u>

<u>TGT</u>GGTCTCC AATGGAGAGC TCCAAGGAAT TGTCTCCTGG GGCTATGGCT

GTGCCCAGAA GAACAGGCCT GGAGTCTACA CCAAGGTCTA CAACTATGTG

GACTGGATTA AGGACACCAT AGCTGCCAAC AGCTAA

PRSS2 S200T Nucleotide (Active site: 194-205 200T)

-continued (SEQ ID NO: 23)

ATGAATCTAC TTCTGATCCT TACCTTTGTT GCAGCTGCTG TTGCTGCCCC

CTTTGATGAT GATGACAAGA TCGTTGGGGG CTACATCTGT GAGGAGAATT

CTGTCCCCTA CCAGGTGTCC TTGAATTCTG GCTACCACTT CTGCGGTGGC

TCCCTCATCA GCGAACAGTG GGTGGTGTCA GCAGGTCACT GCTACAAGTC

GGCAATTAAC TCAAAATTAT CAGGAAGAGG GTGTGAATAT CACCGCATCC

AGGTGAGACT GGGAGAGCAC AACATCGAAG TCCTGGAGGG GAATGAACAG

TTCATCAATG CGGCCAAGAT CATCCGCCAC CCCAAATACA ACAGCCGGAC

TCTGGACAAT GACATCCTGC TGATCAAGCT CTCCTCACCT GCCGTCATCA

ATTCCCGCGT GTCCGCCATC TCTCTGCCCA CTGCCCCTCC AGCTGCTGGC

ACCGAGTCCC TCATCTCCGG CTGGGGCAAC ACTCTGAGTT CTGGTGCCGA

CTACCCAGAC GAGCTGCAGT GCCTGGATGC TCCTGTGCTG AGCCAGGCTG

AGTGTGAAGC CTCCTACCCT GAGAAGATTA CCAACAACAT GTTCTGTGTG

GGCTTCCTCG AGGGAGGCAA GGATTCCTGC CAGGGTGATA CTGGTGGCCC

TGTGGTCTCC AATGGAGAGC TCCAAGGAAT TGTCTCCTGG GGCTATGGCT

GTGCCCAGAA GAACAGGCCT GGAGTCTACA CCAAGGTCTA CAACTATGTG

GACTGGATTA AGGACACCAT AGCTGCCAAC AGCTAA

PRSS2 S200C Nucleotide (Active site: 194-205 200C)

(SEQ ID NO: 24)

ATGAATCTAC TTCTGATCCT TACCTTTGTT GCAGCTGCTG TTGCTGCCCC

CTTTGATGAT GATGACAAGA TCGTTGGGGG CTACATCTGT GAGGAGAATT

CTGTCCCCTA CCAGGTGTCC TTGAATTCTG GCTACCACTT CTGCGGTGGC

TCCCTCATCA GCGAACAGTG GGTGGTGTCA GCAGGTCACT GCTACAAGTC

GGCAATTAAC TCAAAATTAT CAGGAAGAGG GTGTGAATAT CACCGCATCC

AGGTGAGACT GGGAGAGCAC AACATCGAAG TCCTGGAGGG GAATGAACAG

TTCATCAATG CGGCCAAGAT CATCCGCCAC CCCAAATACA ACAGCCGGAC

TCTGGACAAT GACATCCTGC TGATCAAGCT CTCCTCACCT GCCGTCATCA

ATTCCCGCGT GTCCGCCATC TCTCTGCCCA CTGCCCCTCC AGCTGCTGGC

ACCGAGTCCC TCATCTCCGG CTGGGGCAAC ACTCTGAGTT CTGGTGCCGA

CTACCCAGAC GAGCTGCAGT GCCTGGATGC TCCTGTGCTG AGCCAGGCTG

AGTGTGAAGC CTCCTACCCT GAGAAGATTA CCAACAACAT GTTCTGTGTG

GGCTTCCTCG AGGGAGGCAA GGATTCCTGC CAGGGTGATT GTGGTGGCCC

TGTGGTCTCC AATGGAGAGC TCCAAGGAAT TGTCTCCTGG GGCTATGGCT

GTGCCCAGAA GAACAGGCCT GGAGTCTACA CCAAGGTCTA CAACTATGTG

GACTGGATTA AGGACACCAT AGCTGCCAAC AGCTAA

REFERENCES

1. Fidler, I. J., *The pathogenesis of cancer metastasis: the 'seed and soil' hypothesis revisited*. Nat Rev Cancer, 2003. 3(6): p. 453-8.
2. Kang, S. Y., et al., *Prosaposin inhibits tumor metastasis via paracrine and endocrine stimulation of stromal p53 and Tsp-1*. Proc Natl Acad Sci USA, 2009. 106(29): p. 12115-20.
3. Lamy, L., et al., *Interactions between CD47 and thrombospondin reduce inflammation*. Journal of Immunology (Baltimore, Md.: 1950), 2007. 178(9): p. 5930-9.
4. Salajegheh, M., et al., *Upregulation of thrombospondin-1(TSP-1) and its binding partners, CD36 and CD47, in sporadic inclusion body myositis*. J Neuroimmunol. 2007. 187(1-2): p. 166-74.
5. Vallejo, A. N., et al., *Central role of thrombospondin-1 in the activation and clonal expansion of inflammatory T cells*. Journal of Immunology (Baltimore, Md.: 1950), 2000. 164(6): p. 2947-54.
6. Catena, R., et al., *Bone marrow-derived Gr1+ cells can generate a metastasis-resistant microenvironment via induced secretion of thrombospondin*-1. Cancer Discov, 2013. 3(5): p. 578-89.

7. Feig, C., et al., *The pancreas cancer microenvironment.* Clin Cancer Res, 2012. 18(16): p. 4266-76.
8. Hiesberger, T., et al., *Cellular uptake of saposin (SAP) precursor and lysosomal delivery by the low density lipoprotein receptor-related protein (LRP).* Embo J, 1998. 17(16): p. 4617-25.
9. Misra, U. K., G. Gawdi, and S. V. Pizzo, *Ligation of low-density lipoprotein receptor-related protein with antibodies elevates intracellular calcium and inositol 1,4,5-trisphosphate in macrophages.* Arch Biochem Biophys, 1999. 372(2): p. 238-47.
10. Mantuano, E., et al., *Low density lipoprotein receptor-related protein (LRP1) regulates Rac1 and RhoA reciprocally to control Schwann cell adhesion and migration.* J Biol Chem, 2010. 285(19): p. 14259-66.
11. Mikhailenko, I., et al., *Recognition of alpha 2-macroglobulin by the low density lipoprotein receptor-related protein requires the cooperation of two ligand binding cluster regions.* J Biol Chem, 2001. 276(42): p. 39484-91.

Without further elaboration, it is believed that one skilled in the art can, based on the above description, utilize the present disclosure to its fullest extent. The specific embodiments are, therefore, to be construed as merely illustrative, and not limitative of the remainder of the disclosure in any way whatsoever. All publications cited herein are incorporated by reference for the purposes or subject matter referenced herein.

The indefinite articles "a" and "an" as used herein in the specification and in the claims, unless clearly indicated to the contrary, should be understood to mean "at least one."

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed:

1. A method of treating cancer, the method comprising administering to a subject in need thereof an effective amount of a polyclonal antibody that binds to amino acids 1-172 Low Density Lipoprotein Receptor-related Protein 1 (LRP1).

2. The method of claim 1, wherein the polyclonal antibody binds to amino acids 151-172 (SEQ ID NO: 3) of LRP1.

3. The method of claim 1, wherein the polyclonal antibody binds to amino acids 140-164 (SEQ ID NO: 18) of LRP1.

4. The method of claim 1, wherein the polyclonal antibody binds to amino acids 151-164 (SEQ ID NO: 19) of LRP1.

5. The method of claim 1, wherein the polyclonal antibody is administered orally, parenterally, intramuscularly, intranasally, intratracheally, intracerebroventricularly, intravenously, or intraperitoneally.

6. The method of claim 1, wherein the cancer is metastatic.

7. The method of claim 1, wherein the cancer is biliary tract cancer; bladder cancer; brain cancer; glioblastoma; medulloblastoma; breast cancer; cervical cancer; choriocarcinoma; colon cancer; endometrial cancer; esophageal cancer; gastric cancer; hematological neoplasm; acute lymphocytic leukemia; myelogenous leukemia; multiple myeloma; AIDS-associated leukemia; adult T-cell leukemia; lymphoma; intraepithelial neoplasm; Bowen's disease; Paget's disease; liver cancer; lung cancer; lymphomas; Hodgkin's disease; lymphocytic lymphoma; neuroblastoma; oral cancer; squamous cell carcinoma; ovarian cancer; pancreatic cancer; prostate cancer; rectal cancer; sarcoma; leiomyosarcoma; rhabdomyosarcoma; liposarcoma; fibrosarcoma; osteosarcoma; skin cancer; testicular cancer; stromal tumor; germ cell tumor; thyroid cancer; or renal cancer.

8. The method of claim 7, wherein the cancer is prostate cancer, breast cancer, ovarian cancer, or pancreatic cancer.

9. The method of claim 1, wherein the polyclonal antibody inhibits the ability of Protease, serine 2 (PRSS2) to repress Tsp-1.

10. The method of claim 1, wherein the polyclonal antibody inhibits binding of PRSS2 to Low Density Lipoprotein Receptor-related Protein 1 (LRP1).

* * * * *

SEQUENCE LISTING

<160> NUMBER OF SEQ ID NOS: 25

<210> SEQ ID NO 1
<211> LENGTH: 4524
<212> TYPE: PRT
<213> ORGANISM: Homo sapiens

<400> SEQUENCE: 1

```
Ile Asp Ala Pro Lys Thr Cys Ser Pro Lys Gln Phe Ala Cys Arg Asp
1               5                   10                  15

Gln Ile Thr Cys Ile Ser Lys Gly Trp Arg Cys Asp Gly Glu Arg Asp
            20                  25                  30

Cys Pro Asp Gly Ser Asp Glu Ala Pro Glu Ile Cys Pro Gln Ser Lys
        35                  40                  45

Ala Gln Arg Cys Gln Pro Asn Glu His Asn Cys Leu Gly Thr Glu Leu
    50                  55                  60

Cys Val Pro Met Ser Arg Leu Cys Asn Gly Val Gln Asp Cys Met Asp
65                  70                  75                  80

Gly Ser Asp Glu Gly Pro His Cys Arg Glu Leu Gln Gly Asn Cys Ser
                85                  90                  95

Arg Leu Gly Cys Gln His His Cys Val Pro Thr Leu Asp Gly Pro Thr
            100                 105                 110

Cys Tyr Cys Asn Ser Ser Phe Gln Leu Gln Ala Asp Gly Lys Thr Cys
        115                 120                 125

Lys Asp Phe Asp Glu Cys Ser Val Tyr Gly Thr Cys Ser Gln Leu Cys
    130                 135                 140

Thr Asn Thr Asp Gly Ser Phe Ile Cys Gly Cys Val Glu Gly Tyr Leu
145                 150                 155                 160

Leu Gln Pro Asp Asn Arg Ser Cys Lys Ala Lys Asn Glu Pro Val Asp
                165                 170                 175

Arg Pro Pro Val Leu Leu Ile Ala Asn Ser Gln Asn Ile Leu Ala Thr
            180                 185                 190

Tyr Leu Ser Gly Ala Gln Val Ser Thr Ile Thr Pro Thr Ser Thr Arg
        195                 200                 205

Gln Thr Thr Ala Met Asp Phe Ser Tyr Ala Asn Glu Thr Val Cys Trp
    210                 215                 220

Val His Val Gly Asp Ser Ala Ala Gln Thr Gln Leu Lys Cys Ala Arg
225                 230                 235                 240
```

-continued

Met Pro Gly Leu Lys Gly Phe Val Asp Glu His Thr Ile Asn Ile Ser
                245                 250                 255

Leu Ser Leu His His Val Glu Gln Met Ala Ile Asp Trp Leu Thr Gly
            260                 265                 270

Asn Phe Tyr Phe Val Asp Asp Ile Asp Asp Arg Ile Phe Val Cys Asn
        275                 280                 285

Arg Asn Gly Asp Thr Cys Val Thr Leu Leu Asp Leu Glu Leu Tyr Asn
    290                 295                 300

Pro Lys Gly Ile Ala Leu Asp Pro Ala Met Gly Lys Val Phe Phe Thr
305                 310                 315                 320

Asp Tyr Gly Gln Ile Pro Lys Val Glu Arg Cys Asp Met Asp Gly Gln
                325                 330                 335

Asn Arg Thr Lys Leu Val Asp Ser Lys Ile Val Phe Pro His Gly Ile
            340                 345                 350

Thr Leu Asp Leu Val Ser Arg Leu Val Tyr Trp Ala Asp Ala Tyr Leu
        355                 360                 365

Asp Tyr Ile Glu Val Val Asp Tyr Glu Gly Lys Gly Arg Gln Thr Ile
    370                 375                 380

Ile Gln Gly Ile Leu Ile Glu His Leu Tyr Gly Leu Thr Val Phe Glu
385                 390                 395                 400

Asn Tyr Leu Tyr Ala Thr Asn Ser Asp Asn Ala Asn Ala Gln Gln Lys
                405                 410                 415

Thr Ser Val Ile Arg Val Asn Arg Phe Asn Ser Thr Glu Tyr Gln Val
            420                 425                 430

Val Thr Arg Val Asp Lys Gly Gly Ala Leu His Ile Tyr His Gln Arg
        435                 440                 445

Arg Gln Pro Arg Val Arg Ser His Ala Cys Glu Asn Asp Gln Tyr Gly
    450                 455                 460

Lys Pro Gly Gly Cys Ser Asp Ile Cys Leu Leu Ala Asn Ser His Lys
465                 470                 475                 480

Ala Arg Thr Cys Arg Cys Arg Ser Gly Phe Ser Leu Gly Ser Asp Gly
                485                 490                 495

Lys Ser Cys Lys Lys Pro Glu His Glu Leu Phe Leu Val Tyr Gly Lys
            500                 505                 510

Gly Arg Pro Gly Ile Ile Arg Gly Met Asp Met Gly Ala Lys Val Pro
        515                 520                 525

Asp Glu His Met Ile Pro Ile Glu Asn Leu Met Asn Pro Arg Ala Leu
    530                 535                 540

Asp Phe His Ala Glu Thr Gly Phe Ile Tyr Phe Ala Asp Thr Thr Ser
545                 550                 555                 560

Tyr Leu Ile Gly Arg Gln Lys Ile Asp Gly Thr Glu Arg Glu Thr Ile
                565                 570                 575

Leu Lys Asp Gly Ile His Asn Val Glu Gly Val Ala Val Asp Trp Met
            580                 585                 590

Gly Asp Asn Leu Tyr Trp Thr Asp Asp Gly Pro Lys Lys Thr Ile Ser
        595                 600                 605

Val Ala Arg Leu Glu Lys Ala Ala Gln Thr Arg Lys Thr Leu Ile Glu
    610                 615                 620

Gly Lys Met Thr His Pro Arg Ala Ile Val Val Asp Pro Leu Asn Gly
625                 630                 635                 640

Trp Met Tyr Trp Thr Asp Trp Glu Glu Asp Pro Lys Asp Ser Arg Arg
                645                 650                 655

Gly Arg Leu Glu Arg Ala Trp Met Asp Gly Ser His Arg Asp Ile Phe

```
                  660               665                 670
    Val Thr Ser Lys Thr Val Leu Trp Pro Asn Gly Leu Ser Leu Asp Ile
              675                 680                 685

Pro Ala Gly Arg Leu Tyr Trp Val Asp Ala Phe Tyr Asp Arg Ile Glu
              690                 695                 700

Thr Ile Leu Leu Asn Gly Thr Asp Arg Lys Ile Val Tyr Glu Gly Pro
    705                 710                 715                 720

Glu Leu Asn His Ala Phe Gly Leu Cys His His Gly Asn Tyr Leu Phe
                        725                 730                 735

Trp Thr Glu Tyr Arg Ser Gly Ser Val Tyr Arg Leu Glu Arg Gly Val
                    740                 745                 750

Gly Gly Ala Pro Pro Thr Val Thr Leu Leu Arg Ser Glu Arg Pro Pro
                755                 760                 765

Ile Phe Glu Ile Arg Met Tyr Asp Ala Gln Gln Gln Val Gly Thr
            770                 775                 780

Asn Lys Cys Arg Val Asn Asn Gly Gly Cys Ser Ser Leu Cys Leu Ala
    785                 790                 795                 800

Thr Pro Gly Ser Arg Gln Cys Ala Cys Ala Glu Asp Gln Val Leu Asp
                    805                 810                 815

Ala Asp Gly Val Thr Cys Leu Ala Asn Pro Ser Tyr Val Pro Pro Pro
                820                 825                 830

Gln Cys Gln Pro Gly Glu Phe Ala Cys Ala Asn Ser Arg Cys Ile Gln
                835                 840                 845

Glu Arg Trp Lys Cys Asp Gly Asp Asn Asp Cys Leu Asp Asn Ser Asp
    850                 855                 860

Glu Ala Pro Ala Leu Cys His Gln His Thr Cys Pro Ser Asp Arg Phe
    865                 870                 875                 880

Lys Cys Glu Asn Asn Arg Cys Ile Pro Asn Arg Trp Leu Cys Asp Gly
                        885                 890                 895

Asp Asn Asp Cys Gly Asn Ser Glu Asp Glu Ser Asn Ala Thr Cys Ser
                    900                 905                 910

Ala Arg Thr Cys Pro Pro Asn Gln Phe Ser Cys Ala Ser Gly Arg Cys
                915                 920                 925

Ile Pro Ile Ser Trp Thr Cys Asp Leu Asp Asp Asp Cys Gly Asp Arg
                930                 935                 940

Ser Asp Glu Ser Ala Ser Cys Ala Tyr Pro Thr Cys Phe Pro Leu Thr
    945                 950                 955                 960

Gln Phe Thr Cys Asn Asn Gly Arg Cys Ile Asn Ile Asn Trp Arg Cys
                    965                 970                 975

Asp Asn Asp Asn Asp Cys Gly Asp Asn Ser Asp Glu Ala Gly Cys Ser
                980                 985                 990

His Ser Cys Ser Ser Thr Gln Phe Lys Cys Asn Ser Gly Arg Cys Ile
                995                1000                1005

Pro Glu His Trp Thr Cys Asp Gly Asp Asn Asp Cys Gly Asp Tyr
    1010                1015                1020

Ser Asp Glu Thr His Ala Asn Cys Thr Asn Gln Ala Thr Arg Pro
    1025                1030                1035

Pro Gly Gly Cys His Thr Asp Glu Phe Gln Cys Arg Leu Asp Gly
    1040                1045                1050

Leu Cys Ile Pro Leu Arg Trp Arg Cys Asp Gly Asp Thr Asp Cys
    1055                1060                1065

Met Asp Ser Ser Asp Glu Lys Ser Cys Glu Gly Val Thr His Val
    1070                1075                1080
```

```
Cys Asp Pro Ser Val Lys Phe Gly Cys Lys Asp Ser Ala Arg Cys
1085                1090                1095

Ile Ser Lys Ala Trp Val Cys Asp Gly Asp Asn Asp Cys Glu Asp
1100                1105                1110

Asn Ser Asp Glu Glu Asn Cys Glu Ser Leu Ala Cys Arg Pro Pro
1115                1120                1125

Ser His Pro Cys Ala Asn Asn Thr Ser Val Cys Leu Pro Pro Asp
1130                1135                1140

Lys Leu Cys Asp Gly Asn Asp Asp Cys Gly Asp Gly Ser Asp Glu
1145                1150                1155

Gly Glu Leu Cys Asp Gln Cys Ser Leu Asn Asn Gly Gly Cys Ser
1160                1165                1170

His Asn Cys Ser Val Ala Pro Gly Glu Gly Ile Val Cys Ser Cys
1175                1180                1185

Pro Leu Gly Met Glu Leu Gly Pro Asp Asn His Thr Cys Gln Ile
1190                1195                1200

Gln Ser Tyr Cys Ala Lys His Leu Lys Cys Ser Gln Lys Cys Asp
1205                1210                1215

Gln Asn Lys Phe Ser Val Lys Cys Ser Cys Tyr Glu Gly Trp Val
1220                1225                1230

Leu Glu Pro Asp Gly Glu Ser Cys Arg Ser Leu Asp Pro Phe Lys
1235                1240                1245

Pro Phe Ile Ile Phe Ser Asn Arg His Glu Ile Arg Arg Ile Asp
1250                1255                1260

Leu His Lys Gly Asp Tyr Ser Val Leu Val Pro Gly Leu Arg Asn
1265                1270                1275

Thr Ile Ala Leu Asp Phe His Leu Ser Gln Ser Ala Leu Tyr Trp
1280                1285                1290

Thr Asp Val Val Glu Asp Lys Ile Tyr Arg Gly Lys Leu Leu Asp
1295                1300                1305

Asn Gly Ala Leu Thr Ser Phe Glu Val Val Ile Gln Tyr Gly Leu
1310                1315                1320

Ala Thr Pro Glu Gly Leu Ala Val Asp Trp Ile Ala Gly Asn Ile
1325                1330                1335

Tyr Trp Val Glu Ser Asn Leu Asp Gln Ile Glu Val Ala Lys Leu
1340                1345                1350

Asp Gly Thr Leu Arg Thr Thr Leu Leu Ala Gly Asp Ile Glu His
1355                1360                1365

Pro Arg Ala Ile Ala Leu Asp Pro Arg Asp Gly Ile Leu Phe Trp
1370                1375                1380

Thr Asp Trp Asp Ala Ser Leu Pro Arg Ile Glu Ala Ala Ser Met
1385                1390                1395

Ser Gly Ala Gly Arg Arg Thr Val His Arg Glu Thr Gly Ser Gly
1400                1405                1410

Gly Trp Pro Asn Gly Leu Thr Val Asp Tyr Leu Glu Lys Arg Ile
1415                1420                1425

Leu Trp Ile Asp Ala Arg Ser Asp Ala Ile Tyr Ser Ala Arg Tyr
1430                1435                1440

Asp Gly Ser Gly His Met Glu Val Leu Arg Gly His Glu Phe Leu
1445                1450                1455

Ser His Pro Phe Ala Val Thr Leu Tyr Gly Gly Glu Val Tyr Trp
1460                1465                1470
```

```
Thr Asp Trp Arg Thr Asn Thr Leu Ala Lys Ala Asn Lys Trp Thr
1475                1480                1485

Gly His Asn Val Thr Val Val Gln Arg Thr Asn Thr Gln Pro Phe
1490                1495                1500

Asp Leu Gln Val Tyr His Pro Ser Arg Gln Pro Met Ala Pro Asn
1505                1510                1515

Pro Cys Glu Ala Asn Gly Gly Gln Gly Pro Cys Ser His Leu Cys
1520                1525                1530

Leu Ile Asn Tyr Asn Arg Thr Val Ser Cys Ala Cys Pro His Leu
1535                1540                1545

Met Lys Leu His Lys Asp Asn Thr Thr Cys Tyr Glu Phe Lys Lys
1550                1555                1560

Phe Leu Leu Tyr Ala Arg Gln Met Glu Ile Arg Gly Val Asp Leu
1565                1570                1575

Asp Ala Pro Tyr Tyr Asn Tyr Ile Ile Ser Phe Thr Val Pro Asp
1580                1585                1590

Ile Asp Asn Val Thr Val Leu Asp Tyr Asp Ala Arg Glu Gln Arg
1595                1600                1605

Val Tyr Trp Ser Asp Val Arg Thr Gln Ala Ile Lys Arg Ala Phe
1610                1615                1620

Ile Asn Gly Thr Gly Val Glu Thr Val Val Ser Ala Asp Leu Pro
1625                1630                1635

Asn Ala His Gly Leu Ala Val Asp Trp Val Ser Arg Asn Leu Phe
1640                1645                1650

Trp Thr Ser Tyr Asp Thr Asn Lys Lys Gln Ile Asn Val Ala Arg
1655                1660                1665

Leu Asp Gly Ser Phe Lys Asn Ala Val Val Gln Gly Leu Glu Gln
1670                1675                1680

Pro His Gly Leu Val Val His Pro Leu Arg Gly Lys Leu Tyr Trp
1685                1690                1695

Thr Asp Gly Asp Asn Ile Ser Met Ala Asn Met Asp Gly Ser Asn
1700                1705                1710

Arg Thr Leu Leu Phe Ser Gly Gln Lys Gly Pro Val Gly Leu Ala
1715                1720                1725

Ile Asp Phe Pro Glu Ser Lys Leu Tyr Trp Ile Ser Ser Gly Asn
1730                1735                1740

His Thr Ile Asn Arg Cys Asn Leu Asp Gly Ser Gly Leu Glu Val
1745                1750                1755

Ile Asp Ala Met Arg Ser Gln Leu Gly Lys Ala Thr Ala Leu Ala
1760                1765                1770

Ile Met Gly Asp Lys Leu Trp Trp Ala Asp Gln Val Ser Glu Lys
1775                1780                1785

Met Gly Thr Cys Ser Lys Ala Asp Gly Ser Gly Ser Val Val Leu
1790                1795                1800

Arg Asn Ser Thr Thr Leu Val Met His Met Lys Val Tyr Asp Glu
1805                1810                1815

Ser Ile Gln Leu Asp His Lys Gly Thr Asn Pro Cys Ser Val Asn
1820                1825                1830

Asn Gly Asp Cys Ser Gln Leu Cys Leu Pro Thr Ser Glu Thr Thr
1835                1840                1845

Arg Ser Cys Met Cys Thr Ala Gly Tyr Ser Leu Arg Ser Gly Gln
1850                1855                1860

Gln Ala Cys Glu Gly Val Gly Ser Phe Leu Leu Tyr Ser Val His
```

```
            1865                1870                1875

Glu Gly Ile Arg Gly Ile Pro Leu Asp Pro Asn Asp Lys Ser Asp
    1880                1885                1890

Ala Leu Val Pro Val Ser Gly Thr Ser Leu Ala Val Gly Ile Asp
    1895                1900                1905

Phe His Ala Glu Asn Asp Thr Ile Tyr Trp Val Asp Met Gly Leu
    1910                1915                1920

Ser Thr Ile Ser Arg Ala Lys Arg Asp Gln Thr Trp Arg Glu Asp
    1925                1930                1935

Val Val Thr Asn Gly Ile Gly Arg Val Glu Gly Ile Ala Val Asp
    1940                1945                1950

Trp Ile Ala Gly Asn Ile Tyr Trp Thr Asp Gln Gly Phe Asp Val
    1955                1960                1965

Ile Glu Val Ala Arg Leu Asn Gly Ser Phe Arg Tyr Val Val Ile
    1970                1975                1980

Ser Gln Gly Leu Asp Lys Pro Arg Ala Ile Thr Val His Pro Glu
    1985                1990                1995

Lys Gly Tyr Leu Phe Trp Thr Glu Trp Gly Gln Tyr Pro Arg Ile
    2000                2005                2010

Glu Arg Ser Arg Leu Asp Gly Thr Glu Arg Val Val Leu Val Asn
    2015                2020                2025

Val Ser Ile Ser Trp Pro Asn Gly Ile Ser Val Asp Tyr Gln Asp
    2030                2035                2040

Gly Lys Leu Tyr Trp Cys Asp Ala Arg Thr Asp Lys Ile Glu Arg
    2045                2050                2055

Ile Asp Leu Glu Thr Gly Glu Asn Arg Glu Val Val Leu Ser Ser
    2060                2065                2070

Asn Asn Met Asp Met Phe Ser Val Ser Val Phe Glu Asp Phe Ile
    2075                2080                2085

Tyr Trp Ser Asp Arg Thr His Ala Asn Gly Ser Ile Lys Arg Gly
    2090                2095                2100

Ser Lys Asp Asn Ala Thr Asp Ser Val Pro Leu Arg Thr Gly Ile
    2105                2110                2115

Gly Val Gln Leu Lys Asp Ile Lys Val Phe Asn Arg Asp Arg Gln
    2120                2125                2130

Lys Gly Thr Asn Val Cys Ala Val Ala Asn Gly Gly Cys Gln Gln
    2135                2140                2145

Leu Cys Leu Tyr Arg Gly Arg Gly Gln Arg Ala Cys Ala Cys Ala
    2150                2155                2160

His Gly Met Leu Ala Glu Asp Gly Ala Ser Cys Arg Glu Tyr Ala
    2165                2170                2175

Gly Tyr Leu Leu Tyr Ser Glu Arg Thr Ile Leu Lys Ser Ile His
    2180                2185                2190

Leu Ser Asp Glu Arg Asn Leu Asn Ala Pro Val Gln Pro Phe Glu
    2195                2200                2205

Asp Pro Glu His Met Lys Asn Val Ile Ala Leu Ala Phe Asp Tyr
    2210                2215                2220

Arg Ala Gly Thr Ser Pro Gly Thr Pro Asn Arg Ile Phe Phe Ser
    2225                2230                2235

Asp Ile His Phe Gly Asn Ile Gln Gln Ile Asn Asp Asp Gly Ser
    2240                2245                2250

Arg Arg Ile Thr Ile Val Glu Asn Val Gly Ser Val Glu Gly Leu
    2255                2260                2265
```

```
Ala Tyr His Arg Gly Trp Asp Thr Leu Tyr Trp Thr Ser Tyr Thr
    2270            2275                2280

Thr Ser Thr Ile Thr Arg His Thr Val Asp Gln Thr Arg Pro Gly
    2285            2290                2295

Ala Phe Glu Arg Glu Thr Val Ile Thr Met Ser Gly Asp Asp His
    2300            2305                2310

Pro Arg Ala Phe Val Leu Asp Glu Cys Gln Asn Leu Met Phe Trp
    2315            2320                2325

Thr Asn Trp Asn Glu Gln His Pro Ser Ile Met Arg Ala Ala Leu
    2330            2335                2340

Ser Gly Ala Asn Val Leu Thr Leu Ile Glu Lys Asp Ile Arg Thr
    2345            2350                2355

Pro Asn Gly Leu Ala Ile Asp His Arg Ala Glu Lys Leu Tyr Phe
    2360            2365                2370

Ser Asp Ala Thr Leu Asp Lys Ile Glu Arg Cys Glu Tyr Asp Gly
    2375            2380                2385

Ser His Arg Tyr Val Ile Leu Lys Ser Glu Pro Val His Pro Phe
    2390            2395                2400

Gly Leu Ala Val Tyr Gly Glu His Ile Phe Trp Thr Asp Trp Val
    2405            2410                2415

Arg Arg Ala Val Gln Arg Ala Asn Lys His Val Gly Ser Asn Met
    2420            2425                2430

Lys Leu Leu Arg Val Asp Ile Pro Gln Gln Pro Met Gly Ile Ile
    2435            2440                2445

Ala Val Ala Asn Asp Thr Asn Ser Cys Glu Leu Ser Pro Cys Arg
    2450            2455                2460

Ile Asn Asn Gly Gly Cys Gln Asp Leu Cys Leu Leu Thr His Gln
    2465            2470                2475

Gly His Val Asn Cys Ser Cys Arg Gly Gly Arg Ile Leu Gln Asp
    2480            2485                2490

Asp Leu Thr Cys Arg Ala Val Asn Ser Ser Cys Arg Ala Gln Asp
    2495            2500                2505

Glu Phe Glu Cys Ala Asn Gly Glu Cys Ile Asn Phe Ser Leu Thr
    2510            2515                2520

Cys Asp Gly Val Pro His Cys Lys Asp Lys Ser Asp Glu Lys Pro
    2525            2530                2535

Ser Tyr Cys Asn Ser Arg Arg Cys Lys Lys Thr Phe Arg Gln Cys
    2540            2545                2550

Ser Asn Gly Arg Cys Val Ser Asn Met Leu Trp Cys Asn Gly Ala
    2555            2560                2565

Asp Asp Cys Gly Asp Gly Ser Asp Glu Ile Pro Cys Asn Lys Thr
    2570            2575                2580

Ala Cys Gly Val Gly Glu Phe Arg Cys Arg Asp Gly Thr Cys Ile
    2585            2590                2595

Gly Asn Ser Ser Arg Cys Asn Gln Phe Val Asp Cys Glu Asp Ala
    2600            2605                2610

Ser Asp Glu Met Asn Cys Ser Ala Thr Asp Cys Ser Ser Tyr Phe
    2615            2620                2625

Arg Leu Gly Val Lys Gly Val Leu Phe Gln Pro Cys Glu Arg Thr
    2630            2635                2640

Ser Leu Cys Tyr Ala Pro Ser Trp Val Cys Asp Gly Ala Asn Asp
    2645            2650                2655
```

```
Cys Gly Asp Tyr Ser Asp Glu Arg Asp Cys Pro Gly Val Lys Arg
        2660            2665            2670

Pro Arg Cys Pro Leu Asn Tyr Phe Ala Cys Pro Ser Gly Arg Cys
        2675            2680            2685

Ile Pro Met Ser Trp Thr Cys Asp Lys Glu Asp Cys Glu His
        2690            2695            2700

Gly Glu Asp Glu Thr His Cys Asn Lys Phe Cys Ser Glu Ala Gln
        2705            2710            2715

Phe Glu Cys Gln Asn His Arg Cys Ile Ser Lys Gln Trp Leu Cys
        2720            2725            2730

Asp Gly Ser Asp Asp Cys Gly Asp Gly Ser Asp Glu Ala Ala His
        2735            2740            2745

Cys Glu Gly Lys Thr Cys Gly Pro Ser Ser Phe Ser Cys Pro Gly
        2750            2755            2760

Thr His Val Cys Val Pro Glu Arg Trp Leu Cys Asp Gly Asp Lys
        2765            2770            2775

Asp Cys Ala Asp Gly Ala Asp Glu Ser Ile Ala Ala Gly Cys Leu
        2780            2785            2790

Tyr Asn Ser Thr Cys Asp Asp Arg Glu Phe Met Cys Gln Asn Arg
        2795            2800            2805

Gln Cys Ile Pro Lys His Phe Val Cys Asp His Asp Arg Asp Cys
        2810            2815            2820

Ala Asp Gly Ser Asp Glu Ser Pro Glu Cys Glu Tyr Pro Thr Cys
        2825            2830            2835

Gly Pro Ser Glu Phe Arg Cys Ala Asn Gly Arg Cys Leu Ser Ser
        2840            2845            2850

Arg Gln Trp Glu Cys Asp Gly Glu Asn Asp Cys His Asp Gln Ser
        2855            2860            2865

Asp Glu Ala Pro Lys Asn Pro His Cys Thr Ser Gln Glu His Lys
        2870            2875            2880

Cys Asn Ala Ser Ser Gln Phe Leu Cys Ser Ser Gly Arg Cys Val
        2885            2890            2895

Ala Glu Ala Leu Leu Cys Asn Gly Gln Asp Asp Cys Gly Asp Ser
        2900            2905            2910

Ser Asp Glu Arg Gly Cys His Ile Asn Glu Cys Leu Ser Arg Lys
        2915            2920            2925

Leu Ser Gly Cys Ser Gln Asp Cys Glu Asp Leu Lys Ile Gly Phe
        2930            2935            2940

Lys Cys Arg Cys Arg Pro Gly Phe Arg Leu Lys Asp Asp Gly Arg
        2945            2950            2955

Thr Cys Ala Asp Val Asp Glu Cys Ser Thr Thr Phe Pro Cys Ser
        2960            2965            2970

Gln Arg Cys Ile Asn Thr His Gly Ser Tyr Lys Cys Leu Cys Val
        2975            2980            2985

Glu Gly Tyr Ala Pro Arg Gly Gly Asp Pro His Ser Cys Lys Ala
        2990            2995            3000

Val Thr Asp Glu Glu Pro Phe Leu Ile Phe Ala Asn Arg Tyr Tyr
        3005            3010            3015

Leu Arg Lys Leu Asn Leu Asp Gly Ser Asn Tyr Thr Leu Leu Lys
        3020            3025            3030

Gln Gly Leu Asn Asn Ala Val Ala Leu Asp Phe Asp Tyr Arg Glu
        3035            3040            3045

Gln Met Ile Tyr Trp Thr Asp Val Thr Thr Gln Gly Ser Met Ile
```

```
            3050                3055                3060
Arg Arg Met His Leu Asn Gly Ser Asn Val Gln Val Leu His Arg
     3065                3070                3075
Thr Gly Leu Ser Asn Pro Asp Gly Leu Ala Val Asp Trp Val Gly
     3080                3085                3090
Gly Asn Leu Tyr Trp Cys Asp Lys Gly Arg Asp Thr Ile Glu Val
     3095                3100                3105
Ser Lys Leu Asn Gly Ala Tyr Arg Thr Val Leu Val Ser Ser Gly
     3110                3115                3120
Leu Arg Glu Pro Arg Ala Leu Val Val Asp Val Gln Asn Gly Tyr
     3125                3130                3135
Leu Tyr Trp Thr Asp Trp Gly Asp His Ser Leu Ile Gly Arg Ile
     3140                3145                3150
Gly Met Asp Gly Ser Ser Arg Ser Val Ile Val Asp Thr Lys Ile
     3155                3160                3165
Thr Trp Pro Asn Gly Leu Thr Leu Asp Tyr Val Thr Glu Arg Ile
     3170                3175                3180
Tyr Trp Ala Asp Ala Arg Glu Asp Tyr Ile Glu Phe Ala Ser Leu
     3185                3190                3195
Asp Gly Ser Asn Arg His Val Val Leu Ser Gln Asp Ile Pro His
     3200                3205                3210
Ile Phe Ala Leu Thr Leu Phe Glu Asp Tyr Val Tyr Trp Thr Asp
     3215                3220                3225
Trp Glu Thr Lys Ser Ile Asn Arg Ala His Lys Thr Thr Gly Thr
     3230                3235                3240
Asn Lys Thr Leu Leu Ile Ser Thr Leu His Arg Pro Met Asp Leu
     3245                3250                3255
His Val Phe His Ala Leu Arg Gln Pro Asp Val Pro Asn His Pro
     3260                3265                3270
Cys Lys Val Asn Asn Gly Gly Cys Ser Asn Leu Cys Leu Leu Ser
     3275                3280                3285
Pro Gly Gly Gly His Lys Cys Ala Cys Pro Thr Asn Phe Tyr Leu
     3290                3295                3300
Gly Ser Asp Gly Arg Thr Cys Val Ser Asn Cys Thr Ala Ser Gln
     3305                3310                3315
Phe Val Cys Lys Asn Asp Lys Cys Ile Pro Phe Trp Trp Lys Cys
     3320                3325                3330
Asp Thr Glu Asp Asp Cys Gly Asp His Ser Asp Glu Pro Pro Asp
     3335                3340                3345
Cys Pro Glu Phe Lys Cys Arg Pro Gly Gln Phe Gln Cys Ser Thr
     3350                3355                3360
Gly Ile Cys Thr Asn Pro Ala Phe Ile Cys Asp Gly Asp Asn Asp
     3365                3370                3375
Cys Gln Asp Asn Ser Asp Glu Ala Asn Cys Asp Ile His Val Cys
     3380                3385                3390
Leu Pro Ser Gln Phe Lys Cys Thr Asn Thr Asn Arg Cys Ile Pro
     3395                3400                3405
Gly Ile Phe Arg Cys Asn Gly Gln Asp Asn Cys Gly Asp Gly Glu
     3410                3415                3420
Asp Glu Arg Asp Cys Pro Glu Val Thr Cys Ala Pro Asn Gln Phe
     3425                3430                3435
Gln Cys Ser Ile Thr Lys Arg Cys Ile Pro Arg Val Trp Val Cys
     3440                3445                3450
```

-continued

```
Asp Arg Asp Asn Asp Cys Val Asp Gly Ser Asp Glu Pro Ala Asn
3455                3460                3465

Cys Thr Gln Met Thr Cys Gly Val Asp Glu Phe Arg Cys Lys Asp
    3470                3475                3480

Ser Gly Arg Cys Ile Pro Ala Arg Trp Lys Cys Asp Gly Glu Asp
        3485                3490                3495

Asp Cys Gly Asp Gly Ser Asp Glu Pro Lys Glu Glu Cys Asp Glu
    3500                3505                3510

Arg Thr Cys Glu Pro Tyr Gln Phe Arg Cys Lys Asn Asn Arg Cys
        3515                3520                3525

Val Pro Gly Arg Trp Gln Cys Asp Tyr Asp Asn Asp Cys Gly Asp
    3530                3535                3540

Asn Ser Asp Glu Glu Ser Cys Thr Pro Arg Pro Cys Ser Glu Ser
    3545                3550                3555

Glu Phe Ser Cys Ala Asn Gly Arg Cys Ile Ala Gly Arg Trp Lys
    3560                3565                3570

Cys Asp Gly Asp His Asp Cys Ala Asp Gly Ser Asp Glu Lys Asp
    3575                3580                3585

Cys Thr Pro Arg Cys Asp Met Asp Gln Phe Gln Cys Lys Ser Gly
    3590                3595                3600

His Cys Ile Pro Leu Arg Trp Arg Cys Asp Ala Asp Ala Asp Cys
    3605                3610                3615

Met Asp Gly Ser Asp Glu Glu Ala Cys Gly Thr Gly Val Arg Thr
    3620                3625                3630

Cys Pro Leu Asp Glu Phe Gln Cys Asn Asn Thr Leu Cys Lys Pro
    3635                3640                3645

Leu Ala Trp Lys Cys Asp Gly Glu Asp Asp Cys Gly Asp Asn Ser
    3650                3655                3660

Asp Glu Asn Pro Glu Glu Cys Ala Arg Phe Val Cys Pro Pro Asn
    3665                3670                3675

Arg Pro Phe Arg Cys Lys Asn Asp Arg Val Cys Leu Trp Ile Gly
    3680                3685                3690

Arg Gln Cys Asp Gly Thr Asp Asn Cys Gly Asp Gly Thr Asp Glu
    3695                3700                3705

Glu Asp Cys Glu Pro Pro Thr Ala His Thr Thr His Cys Lys Asp
    3710                3715                3720

Lys Lys Glu Phe Leu Cys Arg Asn Gln Arg Cys Leu Ser Ser Ser
    3725                3730                3735

Leu Arg Cys Asn Met Phe Asp Asp Cys Gly Asp Gly Ser Asp Glu
    3740                3745                3750

Glu Asp Cys Ser Ile Asp Pro Lys Leu Thr Ser Cys Ala Thr Asn
    3755                3760                3765

Ala Ser Ile Cys Gly Asp Glu Ala Arg Cys Val Arg Thr Glu Lys
    3770                3775                3780

Ala Ala Tyr Cys Ala Cys Arg Ser Gly Phe His Thr Val Pro Gly
    3785                3790                3795

Gln Pro Gly Cys Gln Asp Ile Asn Glu Cys Leu Arg Phe Gly Thr
    3800                3805                3810

Cys Ser Gln Leu Cys Asn Asn Thr Lys Gly Gly His Leu Cys Ser
    3815                3820                3825

Cys Ala Arg Asn Phe Met Lys Thr His Asn Thr Cys Lys Ala Glu
    3830                3835                3840
```

```
Gly Ser Glu Tyr Gln Val Leu Tyr Ile Ala Asp Asp Asn Glu Ile
    3845                3850                3855

Arg Ser Leu Phe Pro Gly His Pro His Ser Ala Tyr Glu Gln Ala
    3860                3865                3870

Phe Gln Gly Asp Glu Ser Val Arg Ile Asp Ala Met Asp Val His
    3875                3880                3885

Val Lys Ala Gly Arg Val Tyr Trp Thr Asn Trp His Thr Gly Thr
    3890                3895                3900

Ile Ser Tyr Arg Ser Leu Pro Pro Ala Ala Pro Pro Thr Thr Ser
    3905                3910                3915

Asn Arg His Arg Arg Gln Ile Asp Arg Gly Val Thr His Leu Asn
    3920                3925                3930

Ile Ser Gly Leu Lys Met Pro Arg Gly Ile Ala Ile Asp Trp Val
    3935                3940                3945

Ala Gly Asn Val Tyr Trp Thr Asp Ser Gly Arg Asp Val Ile Glu
    3950                3955                3960

Val Ala Gln Met Lys Gly Glu Asn Arg Lys Thr Leu Ile Ser Gly
    3965                3970                3975

Met Ile Asp Glu Pro His Ala Ile Val Val Asp Pro Leu Arg Gly
    3980                3985                3990

Thr Met Tyr Trp Ser Asp Trp Gly Asn His Pro Lys Ile Glu Thr
    3995                4000                4005

Ala Ala Met Asp Gly Thr Leu Arg Glu Thr Leu Val Gln Asp Asn
    4010                4015                4020

Ile Gln Trp Pro Thr Gly Leu Ala Val Asp Tyr His Asn Glu Arg
    4025                4030                4035

Leu Tyr Trp Ala Asp Ala Lys Leu Ser Val Ile Gly Ser Ile Arg
    4040                4045                4050

Leu Asn Gly Thr Asp Pro Ile Val Ala Ala Asp Ser Lys Arg Gly
    4055                4060                4065

Leu Ser His Pro Phe Ser Ile Asp Val Phe Glu Asp Tyr Ile Tyr
    4070                4075                4080

Gly Val Thr Tyr Ile Asn Asn Arg Val Phe Lys Ile His Lys Phe
    4085                4090                4095

Gly His Ser Pro Leu Val Asn Leu Thr Gly Gly Leu Ser His Ala
    4100                4105                4110

Ser Asp Val Val Leu Tyr His Gln His Lys Gln Pro Glu Val Thr
    4115                4120                4125

Asn Pro Cys Asp Arg Lys Lys Cys Glu Trp Leu Cys Leu Leu Ser
    4130                4135                4140

Pro Ser Gly Pro Val Cys Thr Cys Pro Asn Gly Lys Arg Leu Asp
    4145                4150                4155

Asn Gly Thr Cys Val Pro Val Pro Ser Pro Thr Pro Pro Pro Asp
    4160                4165                4170

Ala Pro Arg Pro Gly Thr Cys Asn Leu Gln Cys Phe Asn Gly Gly
    4175                4180                4185

Ser Cys Phe Leu Asn Ala Arg Arg Gln Pro Lys Cys Arg Cys Gln
    4190                4195                4200

Pro Arg Tyr Thr Gly Asp Lys Cys Glu Leu Asp Gln Cys Trp Glu
    4205                4210                4215

His Cys Arg Asn Gly Gly Thr Cys Ala Ala Ser Pro Ser Gly Met
    4220                4225                4230

Pro Thr Cys Arg Cys Pro Thr Gly Phe Thr Gly Pro Lys Cys Thr
```

-continued

```
            4235                4240                4245

Gln Gln Val Cys Ala Gly Tyr Cys Ala Asn Asn Ser Thr Cys Thr
        4250                4255                4260

Val Asn Gln Gly Asn Gln Pro Gln Cys Arg Cys Leu Pro Gly Phe
    4265                4270                4275

Leu Gly Asp Arg Cys Gln Tyr Arg Gln Cys Ser Gly Tyr Cys Glu
4280                4285                4290

Asn Phe Gly Thr Cys Gln Met Ala Ala Asp Gly Ser Arg Gln Cys
    4295                4300                4305

Arg Cys Thr Ala Tyr Phe Glu Gly Ser Arg Cys Glu Val Asn Lys
4310                4315                4320

Cys Ser Arg Cys Leu Glu Gly Ala Cys Val Val Asn Lys Gln Ser
    4325                4330                4335

Gly Asp Val Thr Cys Asn Cys Thr Asp Gly Arg Val Ala Pro Ser
    4340                4345                4350

Cys Leu Thr Cys Val Gly His Cys Ser Asn Gly Gly Ser Cys Thr
    4355                4360                4365

Met Asn Ser Lys Met Met Pro Glu Cys Gln Cys Pro Pro His Met
    4370                4375                4380

Thr Gly Pro Arg Cys Glu Glu His Val Phe Ser Gln Gln Gln Pro
    4385                4390                4395

Gly His Ile Ala Ser Ile Leu Ile Pro Leu Leu Leu Leu Leu Leu
    4400                4405                4410

Leu Val Leu Val Ala Gly Val Val Phe Trp Tyr Lys Arg Arg Val
    4415                4420                4425

Gln Gly Ala Lys Gly Phe Gln His Gln Arg Met Thr Asn Gly Ala
    4430                4435                4440

Met Asn Val Glu Ile Gly Asn Pro Thr Tyr Lys Met Tyr Glu Gly
    4445                4450                4455

Gly Glu Pro Asp Asp Val Gly Gly Leu Leu Asp Ala Asp Phe Ala
    4460                4465                4470

Leu Asp Pro Asp Lys Pro Thr Asn Phe Thr Asn Pro Val Tyr Ala
    4475                4480                4485

Thr Leu Tyr Met Gly Gly His Gly Ser Arg His Ser Leu Ala Ser
    4490                4495                4500

Thr Asp Glu Lys Arg Glu Leu Leu Gly Arg Gly Pro Glu Asp Glu
    4505                4510                4515

Ile Gly Asp Pro Leu Ala
    4520

<210> SEQ ID NO 2
<211> LENGTH: 172
<212> TYPE: PRT
<213> ORGANISM: Artificial Sequence
<220> FEATURE:
<223> OTHER INFORMATION: Synthetic Polypeptide

<400> SEQUENCE: 2

Ile Asp Ala Pro Lys Thr Cys Ser Pro Lys Gln Phe Ala Cys Arg Asp
1               5                   10                  15

Gln Ile Thr Cys Ile Ser Lys Gly Trp Arg Cys Asp Gly Glu Arg Asp
            20                  25                  30

Cys Pro Asp Gly Ser Asp Glu Ala Pro Glu Ile Cys Pro Gln Ser Lys
        35                  40                  45

Ala Gln Arg Cys Gln Pro Asn Glu His Asn Cys Leu Gly Thr Glu Leu
```

```
                    50                  55                  60
Cys Val Pro Met Ser Arg Leu Cys Asn Gly Val Gln Asp Cys Met Asp
 65                  70                  75                  80

Gly Ser Asp Glu Gly Pro His Cys Arg Glu Leu Gln Gly Asn Cys Ser
                 85                  90                  95

Arg Leu Gly Cys Gln His His Cys Val Pro Thr Leu Asp Gly Pro Thr
            100                 105                 110

Cys Tyr Cys Asn Ser Ser Phe Gln Leu Gln Ala Asp Gly Lys Thr Cys
        115                 120                 125

Lys Asp Phe Asp Glu Cys Ser Val Tyr Gly Thr Cys Ser Gln Leu Cys
    130                 135                 140

Thr Asn Thr Asp Gly Ser Phe Ile Cys Gly Cys Val Glu Gly Tyr Leu
145                 150                 155                 160

Leu Gln Pro Asp Asn Arg Ser Cys Lys Ala Lys Asn
                165                 170

<210> SEQ ID NO 3
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 3

Phe Ile Cys Gly Cys Val Glu Gly Tyr Leu Leu Gln Pro Asp Asn Arg
 1               5                  10                  15

Ser Cys Lys Ala Lys Asn
            20

<210> SEQ ID NO 4
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 4
ccggtctgag ttctggtgcc gactactcga gtagtcggca ccagaactca gatttttg        58

<210> SEQ ID NO 5
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 5
ccggacagct tcctgagggc taattctcga gaattagccc tcaggaagct gttttttg        58

<210> SEQ ID NO 6
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 6
ccgggatccg tgtgaaccgc tttaactcga gttaaagcgg ttcacacgga tcttttg         58

<210> SEQ ID NO 7
<211> LENGTH: 25
<212> TYPE: PRT
```

<213> ORGANISM: Artificial Sequence
<220> FEATURE:
<223> OTHER INFORMATION: Synthetic Polypeptide

<400> SEQUENCE: 7

```
Ile Asp Ala Pro Lys Thr Cys Ser Pro Lys Gln Phe Ala Cys Arg Asp
1               5                   10                  15

Gln Ile Thr Cys Ile Ser Lys Gly Trp
            20                  25
```

<210> SEQ ID NO 8
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 8

```
Arg Asp Gln Ile Thr Cys Ile Ser Lys Gly Trp Arg Cys Asp Gly Glu
1               5                   10                  15

Arg Asp Cys Pro Asp Gly Ser Asp Glu
            20                  25
```

<210> SEQ ID NO 9
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 9

```
Arg Cys Asp Gly Glu Arg Asp Cys Pro Asp Gly Ser Asp Glu Ala Pro
1               5                   10                  15

Glu Ile Cys Pro Gln Ser Lys Ala Gln
            20                  25
```

<210> SEQ ID NO 10
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 10

```
Ala Pro Glu Ile Cys Pro Gln Ser Lys Ala Gln Arg Cys Gln Pro Asn
1               5                   10                  15

Glu His Asn Cys Leu Gly Thr Glu Leu
            20                  25
```

<210> SEQ ID NO 11
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 11

```
Arg Cys Gln Pro Asn Glu His Asn Cys Leu Gly Thr Glu Leu Cys Val
1               5                   10                  15

Pro Met Ser Arg Leu Cys Asn Gly Val
            20                  25
```

<210> SEQ ID NO 12
<211> LENGTH: 25

<212> TYPE: PRT
<213> ORGANISM: Artificial Sequence
<220> FEATURE:
<223> OTHER INFORMATION: Synthetic Polypeptide

<400> SEQUENCE: 12

Thr Glu Leu Cys Val Pro Met Ser Arg Leu Cys Asn Gly Val Gln Asp
1               5                   10                  15

Cys Met Asp Gly Ser Asp Glu Gly Pro
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 13

Gln Asp Cys Met Asp Gly Ser Asp Glu Gly Pro His Cys Arg Glu Leu
1               5                   10                  15

Gln Gly Asn Cys Ser Arg Leu Gly Cys
            20                  25

<210> SEQ ID NO 14
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 14

His Cys Arg Glu Leu Gln Gly Asn Cys Ser Arg Leu Gly Cys Gln His
1               5                   10                  15

His Cys Val Pro Thr Leu Asp Gly Pro
            20                  25

<210> SEQ ID NO 15
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 15

Gln His His Cys Val Pro Thr Leu Asp Gly Pro Thr Cys Tyr Cys Asn
1               5                   10                  15

Ser Ser Phe Gln Leu Gln Ala Asp Gly Lys Thr
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 16

Thr Cys Tyr Cys Asn Ser Ser Phe Gln Leu Gln Ala Asp Gly Lys Thr
1               5                   10                  15

Cys Lys Asp Phe Asp Glu Cys Ser Val
            20                  25

<210> SEQ ID NO 17

```
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 17

Lys Thr Cys Lys Asp Phe Asp Glu Cys Ser Val Tyr Gly Thr Cys Ser
1               5                   10                  15

Gln Leu Cys Thr Asn Thr Asp Gly Ser
            20                  25

<210> SEQ ID NO 18
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 18

Tyr Gly Thr Cys Ser Gln Leu Cys Thr Asn Thr Asp Gly Ser Phe Ile
1               5                   10                  15

Cys Gly Cys Val Glu Gly Tyr Leu Leu
            20                  25

<210> SEQ ID NO 19
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 19

Phe Ile Cys Gly Cys Val Glu Gly Tyr Leu Leu
1               5                   10

<210> SEQ ID NO 20
<211> LENGTH: 786
<212> TYPE: DNA
<213> ORGANISM: Artificial Sequence
<220> FEATURE:
<223> OTHER INFORMATION: Synthetic Polynucleotide

<400> SEQUENCE: 20
atgaatctac ttctgatcct tacctttgtt gcagctgctg ttgctgcccc ctttgatgat      60
gatgacaaga tcgttggggg ctacatctgt gaggagaatt ctgtccccta ccaggtgtcc     120
ttgaattctg ctaccacttc tgcggtggc tccctcatca gcgaacagtg ggtggtgtca     180
gcaggtcact gctacaagtc ggcaattaac tcaaaattat caggaagagg gtgtgaatat     240
caccgcatcc aggtgagact gggagagcac aacatcgaag tcctggaggg gaatgaacag     300
ttcatcaatg cggccaagat catccgccac cccaaataca acagccggac tctggacaat     360
gacatcctgc tgatcaagct ctcctcacct gccgtcatca attcccgcgt gtccgccatc     420
tctctgccca ctgcccctcc agctgctggc accgagtccc tcatctccgg ctggggcaac     480
actctgagtt ctggtgccga ctacccagac gagctgcagt gcctggatgc tcctgtgctg     540
agccaggctg agtgtgaagc ctcctaccct gagaagatta ccaacaacat gttctgtgtg     600
ggcttcctcg agggaggcaa ggattcctgc caggtgatt ctggtggccc tgtggtctcc     660
aatggagagc tccaaggaat tgtctcctgg ggctatggct gtgcccagaa gaacaggcct     720
ggagtctaca ccaaggtcta caactatgtg gactggatta aggacaccat agctgccaac     780
```

<210> SEQ ID NO 21
<211> LENGTH: 786
<212> TYPE: DNA
<213> ORGANISM: Artificial Sequence
<220> FEATURE:
<223> OTHER INFORMATION: Synthetic Polynucleotide

<400> SEQUENCE: 21

```
atgaatctac ttctgatcct tacctttgtt gcagctgctg ttgctgcccc ctttgatgat      60
gatgacaaga tcgttggggg ctacatctgt gaggagaatt ctgtcccta ccaggtgtcc      120
ttgaattctg gctaccactt ctgcggtggc tccctcatca gcgaacagtg ggtggtgtca     180
gcaggtcact gctacaagtc ggcaattaac tcaaaattat caggaagagg gtgtgaatat     240
caccgcatcc aggtgagact gggagagcac aacatcgaag tcctggaggg gaatgaacag    300
ttcatcaatg cggccaagat catccgccac cccaaataca acagccggac tctggacaat    360
gacatcctgc tgatcaagct ctcctcacct gccgtcatca attcccgcgt gtccgccatc    420
tctctgccca ctgcccctcc agctgctggc accgagtccc tcatctccgg ctggggcaac    480
actctgagtt ctggtgccga ctacccagac gagctgcagt gcctggatgc tcctgtgctg    540
agccaggctg agtgtgaagc ctcctaccct gagaagatta ccaacaacat gttctgtgtg    600
ggcttcctcg agcgaggcaa ggattcctgc aggtgattg ctggtggccc tgtggtctcc    660
aatggagagc tccaaggaat tgtctcctgg ggctatggct gtgcccagaa gaacaggcct    720
ggagtctaca ccaaggtcta caactatgtg gactggatta aggacaccat agctgccaac    780
agctaa                                                                786
```

<210> SEQ ID NO 22
<211> LENGTH: 786
<212> TYPE: DNA
<213> ORGANISM: Artificial Sequence
<220> FEATURE:
<223> OTHER INFORMATION: Synthetic Polynucleotide

<400> SEQUENCE: 22

```
atgaatctac ttctgatcct tacctttgtt gcagctgctg ttgctgcccc ctttgatgat      60
gatgacaaga tcgttggggg ctacatctgt gaggagaatt ctgtcccta ccaggtgtcc     120
ttgaattctg gctaccactt ctgcggtggc tccctcatca gcgaacagtg ggtggtgtca    180
gcaggtcact gctacaagtc ggcaattaac tcaaaattat caggaagagg gtgtgaatat    240
caccgcatcc aggtgagact gggagagcac aacatcgaag tcctggaggg gaatgaacag   300
ttcatcaatg cggccaagat catccgccac cccaaataca acagccggac tctggacaat   360
gacatcctgc tgatcaagct ctcctcacct gccgtcatca attcccgcgt gtccgccatc   420
tctctgccca ctgcccctcc agctgctggc accgagtccc tcatctccgg ctggggcaac   480
actctgagtt ctggtgccga ctacccagac gagctgcagt gcctggatgc tcctgtgctg   540
agccaggctg agtgtgaagc ctcctaccct gagaagatta ccaacaacat gttctgtgtg   600
ggcttcctcg agggaggcaa ggattcctgc aggtgatg ctggtggccc tgtggtctcc    660
aatggagagc tccaaggaat tgtctcctgg ggctatggct gtgcccagaa gaacaggcct   720
ggagtctaca ccaaggtcta caactatgtg gactggatta aggacaccat agctgccaac   780
agctaa                                                               786
```

<210> SEQ ID NO 23
<211> LENGTH: 786
<212> TYPE: DNA
<213> ORGANISM: Artificial Sequence
<220> FEATURE:
<223> OTHER INFORMATION: Synthetic Polynucleotide

<400> SEQUENCE: 23

```
atgaatctac ttctgatcct tacctttgtt gcagctgctg ttgctgcccc ctttgatgat      60
gatgacaaga tcgttggggg ctacatctgt gaggagaatt ctgtcccta ccaggtgtcc     120
ttgaattctg gctaccactt ctgcggtggc tccctcatca gcgaacagtg ggtggtgtca    180
gcaggtcact gctacaagtc ggcaattaac tcaaaattat caggaagagg gtgtgaatat    240
caccgcatcc aggtgagact gggagagcac aacatcgaag tcctggaggg gaatgaacag    300
ttcatcaatg cggccaagat catccgccac cccaaataca cagccggac tctggacaat    360
gacatcctgc tgatcaagct ctcctcacct gccgtcatca attcccgcgt gtccgccatc    420
tctctgccca ctgcccctcc agctgctggc accgagtccc tcatctccgg ctggggcaac    480
actctgagtt ctggtgccga ctacccagac gagctgcagt gcctggatgc tcctgtgctg    540
agccaggctg agtgtgaagc ctcctaccct gagaagatta ccaacaacat gttctgtgtg    600
ggcttcctcg agggaggcaa ggattcctgc caggggtgata ctggtggccc tgtggtctcc    660
aatggagagc tccaaggaat tgtctcctgg ggctatggct gtgcccagaa gaacaggcct    720
ggagtctaca ccaaggtcta caactatgtg gactggatta aggacaccat agctgccaac    780
agctaa                                                                786
```

<210> SEQ ID NO 24
<211> LENGTH: 786
<212> TYPE: DNA
<213> ORGANISM: Artificial Sequence
<220> FEATURE:
<223> OTHER INFORMATION: Synthetic Polynucleotide

<400> SEQUENCE: 24

```
atgaatctac ttctgatcct tacctttgtt gcagctgctg ttgctgcccc ctttgatgat      60
gatgacaaga tcgttggggg ctacatctgt gaggagaatt ctgtcccta ccaggtgtcc     120
ttgaattctg gctaccactt ctgcggtggc tccctcatca gcgaacagtg ggtggtgtca    180
gcaggtcact gctacaagtc ggcaattaac tcaaaattat caggaagagg gtgtgaatat    240
caccgcatcc aggtgagact gggagagcac aacatcgaag tcctggaggg gaatgaacag    300
ttcatcaatg cggccaagat catccgccac cccaaataca cagccggac tctggacaat    360
gacatcctgc tgatcaagct ctcctcacct gccgtcatca attcccgcgt gtccgccatc    420
tctctgccca ctgcccctcc agctgctggc accgagtccc tcatctccgg ctggggcaac    480
actctgagtt ctggtgccga ctacccagac gagctgcagt gcctggatgc tcctgtgctg    540
agccaggctg agtgtgaagc ctcctaccct gagaagatta ccaacaacat gttctgtgtg    600
ggcttcctcg agggaggcaa ggattcctgc caggggtgatt gtggtggccc tgtggtctcc    660
aatggagagc tccaaggaat tgtctcctgg ggctatggct gtgcccagaa gaacaggcct    720
ggagtctaca ccaaggtcta caactatgtg gactggatta aggacaccat agctgccaac    780
agctaa                                                                786
```

<210> SEQ ID NO 25
<211> LENGTH: 207
<212> TYPE: PRT

<213> ORGANISM: Artificial Sequence
<220> FEATURE:
<223> OTHER INFORMATION: Synthetic Polypeptide

<400> SEQUENCE: 25

```
Glu Gln Trp Val Val Ser Ala Gly His Cys Tyr Lys Ser Ala Ile Asn
1               5                   10                  15

Ser Lys Leu Ser Gly Arg Gly Cys Glu Tyr His Arg Ile Gln Val Arg
            20                  25                  30

Leu Gly Glu His Asn Ile Glu Val Leu Glu Gly Asn Glu Gln Phe Ile
        35                  40                  45

Asn Ala Ala Lys Ile Ile Arg His Pro Lys Tyr Asn Ser Arg Thr Leu
    50                  55                  60

Asp Asn Asp Ile Leu Leu Ile Lys Leu Ser Ser Pro Ala Val Ile Asn
65                  70                  75                  80

Ser Arg Val Ser Ala Ile Ser Leu Pro Thr Ala Pro Pro Ala Ala Gly
                85                  90                  95

Thr Glu Ser Leu Ile Ser Gly Trp Gly Asn Thr Leu Ser Ser Gly Ala
            100                 105                 110

Asp Tyr Pro Asp Glu Leu Gln Cys Leu Asp Ala Pro Val Leu Ser Gln
        115                 120                 125

Ala Glu Cys Glu Ala Ser Tyr Pro Gly Lys Ile Thr Asn Asn Met Phe
    130                 135                 140

Cys Val Gly Phe Leu Glu Gly Gly Lys Asp Ser Cys Gln Gly Asp Ser
145                 150                 155                 160

Gly Gly Pro Val Val Ser Asn Gly Glu Leu Gln Gly Ile Val Ser Trp
                165                 170                 175

Gly Tyr Gly Cys Ala Gln Lys Asn Arg Pro Gly Val Tyr Thr Lys Val
            180                 185                 190

Tyr Asn Tyr Val Asp Trp Ile Lys Asp Thr Ile Ala Ala Asn Ser
        195                 200                 205
```

UNITED STATES PATENT AND TRADEMARK OFFICE
CERTIFICATE OF CORRECTION

| | |
|---|---|
| PATENT NO. | : 11,466,080 B2 |
| APPLICATION NO. | : 16/496129 |
| DATED | : October 11, 2022 |
| INVENTOR(S) | : Randolph S. Watnick |

It is certified that error appears in the above-identified patent and that said Letters Patent is hereby corrected as shown below:

In the Specification

At Column 1, Line 12, below the RELATED APPLICATIONS paragraph, please add the following new paragraph:
FEDERALLY SPONSORED RESEARCH
This invention was made with government support under Grant Number CA135417, awarded by the National Institutes of Health. The Government has certain rights in the invention.

In the Claims

At Column 70, Claim 7, Line 47, "disease; liver cancer; lung cancer; lymphomas; Hodgkin's" should read -- disease; liver cancer; lung cancer; Hodgkin's --

Signed and Sealed this
Fourteenth Day of February, 2023

Katherine Kelly Vidal
*Director of the United States Patent and Trademark Office*